US010324309B2

United States Patent
Hyde et al.

(10) Patent No.: US 10,324,309 B2
(45) Date of Patent: *Jun. 18, 2019

(54) MODIFIABLE-FOCUS LENS DEVICES, SYSTEMS, AND RELATED METHODS

(71) Applicant: Elwha LLC, Bellevue, WA (US)

(72) Inventors: Roderick A. Hyde, Redmond, WA (US); Clarence T. Tegreene, Mercer Island, WA (US)

(73) Assignee: ELWHA LLC, Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/074,606

(22) Filed: Mar. 18, 2016

(65) Prior Publication Data

US 2017/0023801 A1    Jan. 26, 2017

Related U.S. Application Data

(63) Continuation-in-part of application No. 14/807,719, filed on Jul. 23, 2015.

(51) Int. Cl.
| | |
|---|---|
| A61F 2/16 | (2006.01) |
| G02C 7/08 | (2006.01) |
| A61B 3/113 | (2006.01) |
| A61B 3/14 | (2006.01) |
| G02C 7/04 | (2006.01) |

(52) U.S. Cl.
CPC .............. *G02C 7/083* (2013.01); *A61B 3/113* (2013.01); *A61B 3/14* (2013.01); *A61F 2/16* (2013.01); *A61F 2/1624* (2013.01); *A61F 2/1627* (2013.01); *G02C 7/041* (2013.01); *G02C 7/08* (2013.01); *A61F 2210/009* (2013.01); *A61F 2250/0002* (2013.01)

(58) Field of Classification Search
CPC .... A61F 2/1627; A61F 2/1635; A61F 2/1654; A61F 2/16; A61F 2210/009
See application file for complete search history.

(56) References Cited

U.S. PATENT DOCUMENTS

| | | | |
|---|---|---|---|
| 5,066,301 | A | 11/1991 | Wiley |
| 5,108,429 | A | 4/1992 | Wiley |
| 5,171,266 | A | 12/1992 | Wiley et al. |
| 5,203,788 | A | 4/1993 | Wiley |
| 5,344,447 | A | 9/1994 | Swanson |
| 6,857,741 | B2 | 2/2005 | Blum et al. |
| 6,871,951 | B2 | 3/2005 | Blum et al. |
| 7,023,594 | B2 | 4/2006 | Blum et al. |

(Continued)

FOREIGN PATENT DOCUMENTS

| | | |
|---|---|---|
| EP | 2 772 791 A1 | 9/2014 |
| WO | WO 2009/153764 A2 | 12/2009 |
| WO | WO 2014/194432 A1 | 12/2014 |

OTHER PUBLICATIONS

U.S. Appl. No. 14/807,719, filed Jul. 23, 2015, Hyde et al.

(Continued)

*Primary Examiner* — Dinah Baria
(74) *Attorney, Agent, or Firm* — Dorsey & Whitney LLP

(57) ABSTRACT

Embodiments disclosed herein are directed to intraocular lens devices, systems, and methods that include determining relative tilt and/or vergence rotation of a subject's eyes and focusing one or more intraocular lenses based on the determined vergence rotation.

49 Claims, 12 Drawing Sheets

(56) References Cited

U.S. PATENT DOCUMENTS

| | | |
|---|---|---|
| 7,396,126 B2 | 7/2008 | Blum et al. |
| 7,475,984 B2 | 1/2009 | Blum et al. |
| 7,517,083 B2 | 4/2009 | Blum et al. |
| 7,832,864 B2 | 11/2010 | Barrett et al. |
| 8,446,341 B2 | 5/2013 | Amirparviz et al. |
| 8,587,734 B2 | 11/2013 | Li |
| 8,608,800 B2 | 12/2013 | Portney |
| 8,885,139 B2 | 11/2014 | Peyghambarian et al. |
| 9,039,179 B2 | 5/2015 | Brown, Jr. et al. |
| 2002/0140899 A1 | 10/2002 | Blum et al. |
| 2003/0210377 A1 | 11/2003 | Blum et al. |
| 2003/0231293 A1 | 12/2003 | Blum et al. |
| 2004/0027501 A1 | 2/2004 | Blum et al. |
| 2005/0140924 A1 | 6/2005 | Blum et al. |
| 2005/0270481 A1 | 12/2005 | Blum et al. |
| 2006/0098164 A1 | 5/2006 | Blum et al. |
| 2006/0164593 A1 | 7/2006 | Peyghambarian et al. |
| 2007/0121065 A1 | 5/2007 | Cox et al. |
| 2008/0106633 A1 | 5/2008 | Blum et al. |
| 2008/0208335 A1 | 8/2008 | Blum et al. |
| 2009/0009717 A1 | 1/2009 | Barrett et al. |
| 2009/0032679 A1 | 2/2009 | Holladay |
| 2009/0105817 A1 | 4/2009 | Bretthauer et al. |
| 2009/0195749 A1 | 8/2009 | Blum et al. |
| 2010/0001926 A1 | 1/2010 | Amirparviz et al. |
| 2010/0225834 A1 | 9/2010 | Li |
| 2010/0324408 A1 | 12/2010 | Klink et al. |
| 2011/0025955 A1 | 2/2011 | Bos et al. |
| 2012/0140167 A1 | 6/2012 | Blum |
| 2013/0035760 A1 | 2/2013 | Portney |
| 2013/0218270 A1 | 8/2013 | Blanckaert et al. |
| 2013/0222756 A1 | 8/2013 | Van Heugten |
| 2014/0085726 A1 | 3/2014 | Portney |
| 2014/0128941 A1 | 5/2014 | Williams |
| 2014/0132904 A1 | 5/2014 | Bos et al. |
| 2014/0156000 A1 | 6/2014 | Campin et al. |
| 2014/0240656 A1 | 8/2014 | Pugh et al. |
| 2015/0057748 A1 | 2/2015 | Azar |
| 2015/0362749 A1* | 12/2015 | Biederman ............ G02C 7/083 351/209 |

OTHER PUBLICATIONS

U.S. Appl. No. 14/807,673, filed Jul. 23, 2015, Hyde et al.
PCT International Search Report; International App. No. PCT/US2016/043065; dated Nov. 4, 2016; pp. 1-3.
PCT International Search Report; International App. No. PCT/US2016/043062; dated Oct. 21, 2016; pp. 1-3.
European Patent Office, Extended European Search Report, Pursuant to Rule 62 EPC; App. No. EP 16828438.8; dated Feb. 28, 2019 (received by our Agent on Mar. 11, 2019); pp. 1-8.
European Patent Office, Extended European search Report, Pursuant to Rule 62 EPC; App. No. 16828440.4; dated Feb. 22, 2019 (recieved by our Agent on Mar. 5, 2019); pp. 1-9.

* cited by examiner

MODIFIABLE-FOCUS LENS DEVICES, SYSTEMS, AND RELATED METHODS

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

This application is a continuation-in-part of U.S. patent application Ser. No. 14/807,719, filed on Jul. 23, 2015.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

BACKGROUND

Focal correction can improve vision of a subject. For example, glasses, contact lenses, and Intraocular lenses (IOLs), such as pseudophakic IOLs, aphikic IOLs, or phakic IOLs (PIOLS), can be used to correct the vision of a subject. Typical IOLs can include monofocal, multifocal, or accommodative configurations. IOLs can include an optic element (e.g., lens) and haptic elements (e.g., arms or wings configured to aid in positioning the IOL).

Such configurations can be limited to focusing either on near or far vision without selectively modifiable adjustment therebetween. Therefore, manufacturers, users, and designers of IOLs continue to seek improved IOLs.

SUMMARY

Embodiments disclosed herein are directed to switchable- and/or modifiable-focus lens (MFL) devices, such as IOL devices, MFL devices (e.g., eyeglasses, goggles, face shields, visors, scopes, such as binoculars, microscopes, etc., with one or more MFLs), systems (including IOL systems), and methods that include determining relative tilt or vergence rotation of a subject's eyes and focusing one or more intraocular lenses based on the determined vergence rotation. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments can be utilized, and other changes can be made, without departing from the spirit or scope of the subject matter presented here.

An embodiment includes a system that includes an eye-vergence detection system configured to detect at least one of a vergence rotation between a first eye and a second eye of a subject or a change in the vergence rotation between the first eye and the second eye of the subject and to generate one or more detection outputs corresponding thereto. The system also includes a switchable lens configured to selectively switch between a first focal length and at least a second focal length that is less than the first focal length. Moreover, the system includes a controller operably coupled to the eye-vergence detection system to receive the one or more detection outputs therefrom. The controller includes control electrical circuitry configured to direct the switchable lens to selectively switch between the first focal length and the second focal length responsive to the one or more detection outputs.

An embodiment includes a system that includes an eye-vergence detection system that has a field source removably positionable on a subject and configured to establish an identifiable field and at least one sensor configured to detect a change in the identifiable field in response to a change in a vergence rotation between a first eye and a second eye of the subject and to generate one or more detection outputs in response thereto. The system also includes at least one switchable lens configured to selectively switch between a first focal length and at least a second focal length that is less than the first focal length. Moreover, the system includes a controller operably coupled to the eye-vergence detection system to receive the one or more detection outputs therefrom. The controller includes control electrical circuitry configured to direct the switchable lens to selectively switch between the first focal length and the second focal length responsive to the one or more detection outputs.

An embodiment includes a system that includes a distance detector positionable on a subject and configured to detect a distance from the subject to an object viewed by the subject and to generate one or more detection outputs corresponding thereto. The system also includes at least one switchable lens configured to selectively switch between a first focal length and at least a second focal length that is less than the first focal length. Moreover, the system includes at least one controller operably coupled to the distance detector to receive the one or more detection outputs therefrom. The at least one controller includes control electrical circuitry configured to direct the switchable lens to selectively switch between the first focal length and the second focal length responsive to the one or more detection outputs.

An embodiment includes a method that includes an eye-vergence detection system detecting at least one of a vergence rotation between a first eye and a second eye of a subject or a change in the vergence rotation between the first eye and the second eye of the subject and generating one or more detection outputs corresponding thereto. The method also includes a switchable lens selectively switching between a first focal length and at least a second focal length that is less than the first focal length. Moreover, the method includes a controller operably coupled to the eye-vergence detection system and receiving the one or more detection outputs therefrom. The controller includes control electrical circuitry directing the switchable lens to selectively switch between the first focal length and the second focal length responsive to the one or more detection outputs.

Features from any of the disclosed embodiments can be used in combination with one another, without limitation. In addition, other features and advantages of the present disclosure will become apparent to those of ordinary skill in the art through consideration of the following detailed description and the accompanying drawings.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 2:
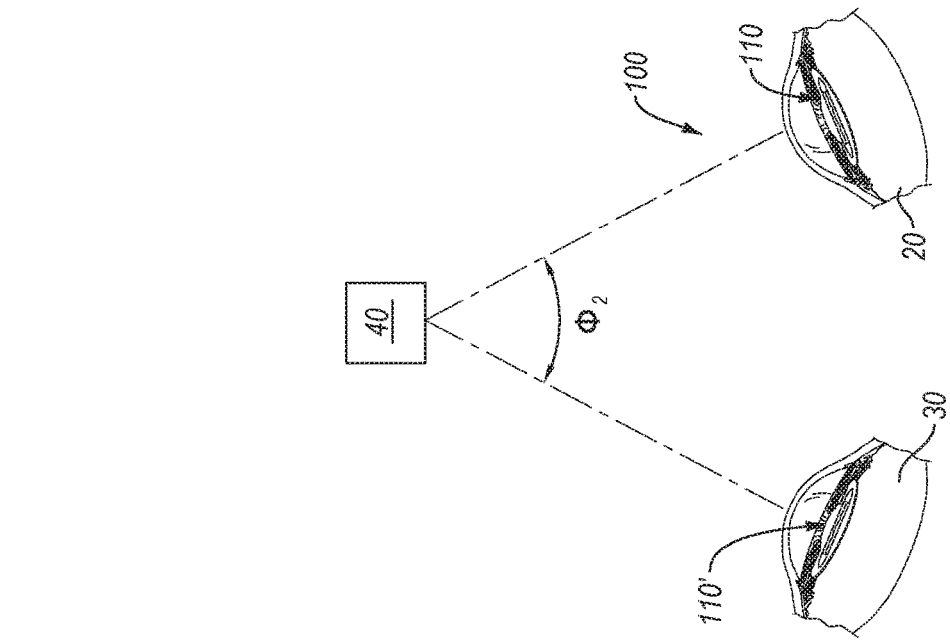
FIG. 2 is a schematic top view of the subject's eyes of FIG. 1, with the eyes having a second vergence therebetween and are focused on a second object at a second distance from the subject that is less than the first distance according to an embodiment.

Embodiments disclosed herein are directed to switchable- and/or modifiable-focus lens (MFL) devices, such as IOL devices, MFL devices (e.g., eyeglasses, goggles, face shields, visors, scopes, such as binoculars, microscopes, etc., with one or more MFLs), systems (including IOL systems), and methods that include determining relative tilt or vergence rotation of a subject's eyes and focusing one or more intraocular lenses based on the determined vergence rotation. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments can be utilized, and other changes can be made, without departing from the spirit or scope of the subject matter presented here.

In one or more embodiments, the MFL systems, such an IOL system, can include at least one MFL device (e.g., IOL device that can be positioned in an eye of a subject), a sensor that can provide or generate an output related to a vergence rotation of the subject's eyes, and a controller that can direct the MFL device to change focal length responsive to the output related to the vergence rotation. For example, the MFL system can include a field source that can establish an identifiable field that can be sensed or detected by the sensor. In an embodiment, the sensor and the identifiable field can have relative locations such that a change in vergence between the eyes (e.g., vergence rotation of the eyes) of the subject produces a change in relative positions or orientations between the sensor and the identifiable field. For example, as the eyes of the subject tilt or pivot, the sensor and the identifiable field can move relative to each other, and the detected changes in the field can be related to a vergence rotation between the eyes of the subject.

In an embodiment, the field can be an identifiable magnetic field established by a permanent or electromagnet. Furthermore, as discussed below in more detail, the field source (e.g., a magnetic field source) can be positioned in at least one eye of the subject. For example, the field source can be embedded in or mounted to an MFL device (e.g., to IOL device) that can be located in one of the subject's eye. Alternatively or additionally, an MFL system can include a field source that is positioned near, but externally to one or both of the subject's eyes (e.g., on subject's eyeglasses). In an embodiment, one or more sensors positioned in one or both eyes of the subject can detect a change in the identifiable field or in a component thereof, during vergence rotation (e.g., as the vergence between the eyes changes), such as when the eyes converge or diverge. Hence, for example, the detected change in an identifiable magnetic field or a component thereof can correspond to a change in the vergence between the eyes.

The MFL system can include a controller. For example, the controller can be operably coupled to the sensor and can receive detection output from the sensor. More specifically, the detection output from the sensor can be based on the detected change in the field or based on the one or more components thereof, which can be related to vergence rotation between the eyes of the subject. In an embodiment, the control can distinguish between vergence rotation of the eyes and co-tilt rotation of the eyes (e.g., when the eyes of the subject tilt in the same direction, such as to view an object located peripherally or to a side of the subject). As a consequence of such distinguishing, in such embodiments each MFL or MFL device (e.g., IOL or IOL device) can act independently of the other, reaching an accurate vergence determination (and hence an accurate focal length determination) on its own, without a need for communication between both MFL devices (e.g., between IOLs). For example, controller can compare each IOL's determined tilt with that of the other IOL in order to decide or determine which portion of each IOL's tilt represents vergence and which represents co-tilt.

In an embodiment, the MFL device (e.g., IOL device) can be switchable between two or more focal lengths (e.g., a first focal length for distance vision and a second focal length for close-up vision). For example, the MFL device can include one or more switchable lenses that can be directed or switched between two or more focal lengths by the controller. Moreover, the controller can be operably connected to the sensor(s) and can receive outputs therefrom, which can be related to the detected change in the field and, hence, to vergence rotation between the eyes. In an embodiment, the controller can switch or direct switching of the MFL device at least partially based on the outputs received from the sensor(s).

Generally, an MFL device can have a selectively modifiable focal length. For example, the MFL can include at least one material that can have electrically-modifiable index of refraction (including any birefringence associated therewith) and/or a diffraction surface defining a diffraction pattern therein, as described more fully in connection with IOLs in U.S. patent application Ser. No. 14/807,673, entitled "intraocular lens systems and related methods," the entire content of which is incorporated herein by this reference. In view of this disclosure, it should be appreciated that the materials, features, elements, and components described in connection with IOLs can be similar to or the same as materials, features, elements, and components of an MFL (e.g., of a lens of MFL in eyeglasses, goggles, face shields, etc.), including but not limited to liquid crystal and electroactive polymer materials.

In an embodiment, the MFL systems disclosed herein can include one or more sensors configured to detect one or more physiological indicia of the subject. For example, an IOL system can include one or more sensors configured to detect glucose concentration, such as in the eye of the subject; eye pressure, heart rate, biological proteins present in the eye, or any other biological indicia. The one or more sensors can be operably coupled to the controller. The controller of the MFL system can be configured to transmit the measurements of the physical indicia to a remote source such as a computer, a cellular phone, or other electronic device. In an embodiment, the measured physical indicia can be used to determine the health of a subject or eye thereof, customize the operation of the MFL device (e.g., of an IOL device) to the particular subject, determine if the MFL controller needs to be removed or adjusted, or determine if the focal adjustments of the MFL controller are suitable for the subject. The electronic device can then transmit instructions to the controller to selectively control or otherwise adjust the functioning of the MFL system, such as controllably changing the focal length of the MFL device.

Figure 1:
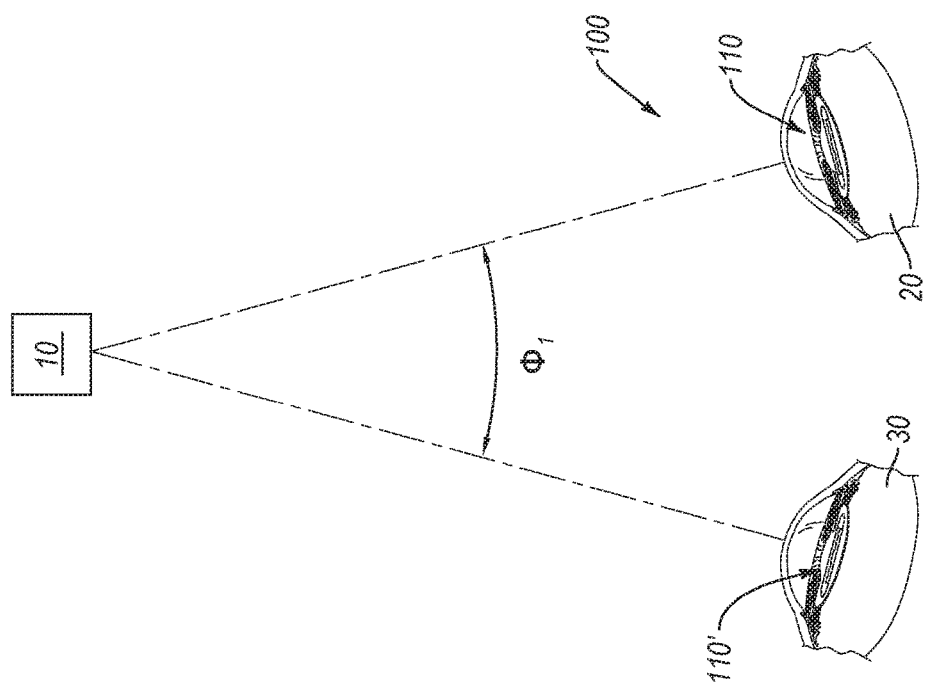
FIG. 1 is a schematic top view of a subject's eyes having a first vergence therebetween and focused on a first object at a first distance from the subject according to an embodiment.

FIG. 1 schematically illustrates eyes 20 and 30 of a subject focused on a first object 10 that is positioned at a first distance from the subject. In particular, when the eyes 20, 30 are focused on the first object 10, an angle between respective optical axes thereof can be at a vergence angle $\phi_1$. FIG. 1 also schematically illustrates an IOL system 100 according to an embodiment. For example, an IOL system 100 can include a first IOL device 110 positioned in a first eye 20 and a second IOL device 110' positioned in a second eye 30 of the subject.

Generally, the first IOL device 110 or the second IOL device 110' can be configured to augment or correct visual deficiencies of the subject or to replace the lenses in the respective first eye 20 or second eye 30 of the subject (e.g., in cataract surgeries). It should be appreciated that, in one or more embodiments, the IOL system 100 can include only a single IOL device (e.g., the first IOL device 110 or the second IOL device 110'), which can be positioned in the first eye 20 or in the second eye 30. The IOL devices 110 or 110' can be switched to or set at a first focal length, such that the light entering the eye from the distance of the first object 10 is focused on the retina of the respective eyes 20, 30, thereby focusing the eyes 20, 30 on the first object 10.

When the subject focuses on another object, such as an object that is closer to the subject than the first object 10, the object's eyes 20, 30 can tilt such as to converge, thereby changing the angle between the optical axes thereof. FIG. 2 schematically shows the subject's eyes 20, 30 focused on a second object 40, which is positioned at a second distance and closer to the subject than the first object 10 (FIG. 1). For example, when the eyes 20, 30 focus on the second object 40, the angle between the optical axis thereof can change to a second angle $\phi_2$. More specifically, as the eyes 20, 30 focus on the closer, second object 40, the eyes 20, 30 converge or in-tilt, such that the second angle $\phi_2$ defined by the respective optical axis thereof is greater than the first angle $\phi_1$.

In an embodiment, responsive to the changed tilt between the eyes 20, 30, the IOL devices 110 or 110' can be switched to the second focal length, which can be shorter than the first focal length. The IOL devices 110 or 110' can include one or more sensors that can sense or detect a change in an identifiable field (e.g., magnetic field) and can correlate that change to the change vergence rotation between the eyes 20, 30 (e.g., convergence to focus on a closer object or divergence to focus on a farther object). Similarly, as the subject attempts to focus eyes 20, 30 on an object at a distance that is greater than the distance to the second object 40 (e.g., on the first object 10 (FIG. 1)), the IOL devices 110 or 110' can be switched to the first focal length (longer than the second focal length).

Moreover, as described below in more detail, the IOL devices 110 or 110' can distinguish between vergence rotation from co-tilt rotation (e.g., when the eyes 20, 30 rotate in the same direction, such as to observe an object located peripherally from the user). As such, for example, the IOL device 110 or 110' can switch focal length responsive to detected vergence rotation. In an embodiment, the IOL devices 110 or 110' can maintain a previously set focal length during co-tilt of the eyes 20, 30.

Figure 3:
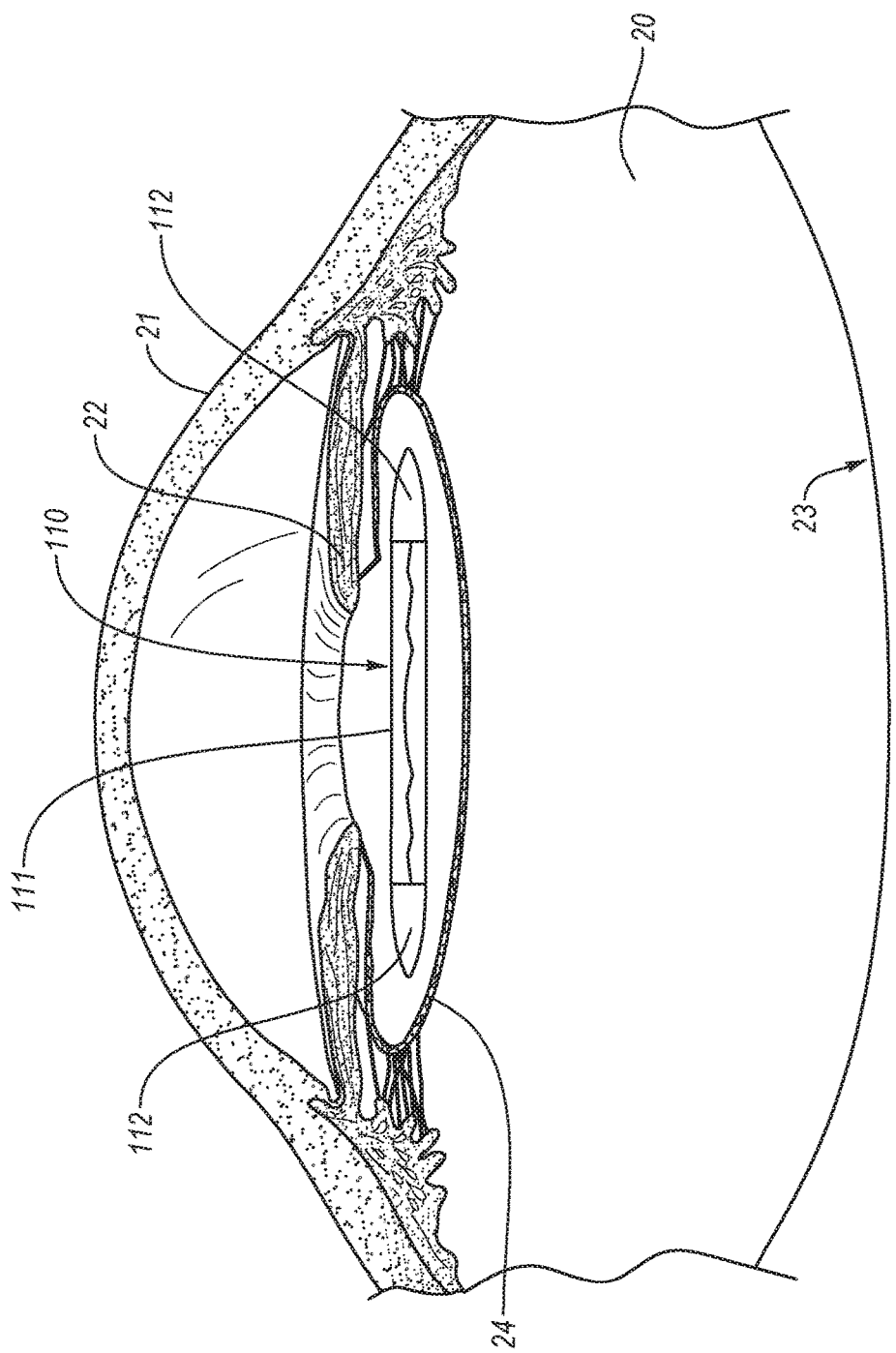
FIG. 3 is a schematic, side, cross-sectional view of a subject's eye and an intraocular lens device located in the eye according to an embodiment.

As mentioned above, the IOL devices 110 or 110' can be located in the subject's eyes (e.g., in the eye 20 or in the eye 30). FIG. 3 is a side, cross-sectional view of the eye 20 with the IOL device 110 implanted therein, according to an embodiment. It should be appreciated that, while the description herein is related to the IOL device 110 and to the corresponding eye 20 of the subject, the IOL device 110' or its location in the eye 30 (FIGS. 1-2) can have the same or similar configuration. Generally, the eye 20 includes a cornea 21, an iris 22, a natural lens, and a retina 23 therebehind. One or more IOL device 110 can be implanted in the eye 20. For example, the IOL device 110 can be implanted over the natural lens, in front of (e.g., in the anterior chamber) or behind the iris 22 (e.g., in the posterior chamber), or internal to the natural lens such as in a capsular bag 24 of the natural lens. In an embodiment, the natural lens can be absent from the eye 20 (e.g., the IOL device 110 can replace the natural lens and can be placed in the anterior chamber, the posterior chamber, or internal to the capsular bag that is used to contain the natural lens).

Generally, as described below in more detail, the IOL device 110 can include a lens 111 and haptics 112 connected to or integrated with the lens 111. In an embodiment, the haptics 112 can be positioned on or secured to one or more structures in the eye 20, thereby positioning or securing the IOL device 110 in the eye 20. For example, the haptics 112 can be positioned on the ciliary body or muscles or in or on the capsular bag 24 of the natural lens. The lens 111 can be located laterally in the center of the eye 20 with the haptics 112 extending laterally therefrom. As mentioned above, the lens 111 of the IOL device 110 can be switched between two or more focal lengths, to focus light entering the eye from a selected distance on the retina 23 of the eye 20, thereby providing a focus on an object located at the selected focal length and augmenting or correcting the vision of the subject.

In an embodiment, the IOL device 110 can be substantially fixed within the eye 20 (e.g., the IOL device can be substantially immobile relative to the optical axis of the eye 20). As such, for example, movement of the eye 20 can result in a corresponding movement of the IOL device 110. In particular, as the eye 20 tilts or pivots in the eye socket, the IOL device 110 can correspondingly tilt or pivot together with the eye 20. Furthermore, one, some, or all of the elements or components of the IOL device 110 can have a predetermined orientation relative to the eye 20 or relative to the optical axis thereof, as described below in more detail.

Figure 4A:
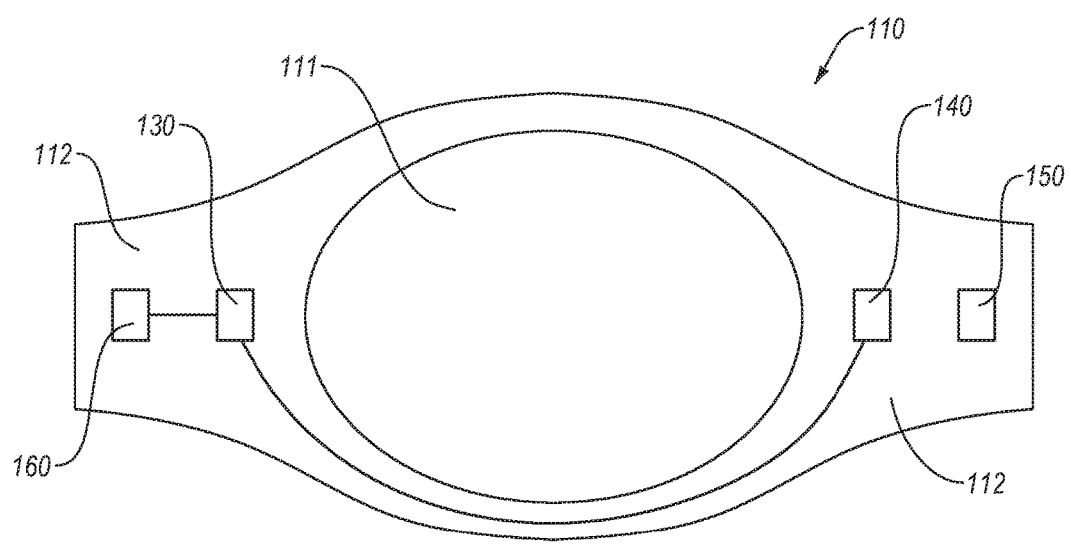
FIG. 4A is a top view of an IOL device located in the eye according to an embodiment.
Figure 4B:
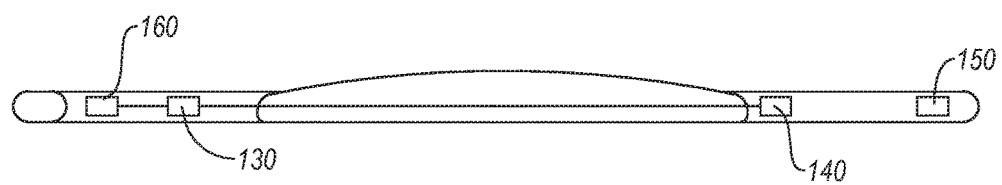
FIG. 4B is a side view of the IOL device of FIG. 4A.

FIGS. 4A and 4B illustrate the IOL device 110 according to an embodiment. FIG. 4A is a top view of the IOL device 110 and FIG. 4B is a side view of the IOL device 110. As described above, the IOL device 110 can be configured to fit in or on one or more anatomical structures of the eye and can include the lens 111 and one or more haptics 112. As shown in FIG. 4A, in an embodiment, the IOL device 110 includes the lens 111. For example, the lens 111 can be configured to focus light onto the surface of the retina and can be substantially circular or elliptical. Furthermore, the lens 111 can be switchable between two or more focal lengths and, in an embodiment, three or more focal lengths.

In an embodiment, the lens 111 can include or can be configured as a switchable diffractive lens. Additionally or alternatively, the lens 111 can include or can be configured as a refractive lens that can have a selectively modifiable index of refraction and focal length (e.g., a variable focus refractive lens). In any embodiment, the lens 111 can be switched at least between the first focal length and at least a second focal length.

In an embodiment, a controller including control electrical circuitry can be operably coupled to the lens 111 and can switch or direct switching of the lens 111 between two or more focal lengths. In an embodiment, the controller can be positioned on or embedded in one or more portions of the IOL device 110. For example, a controller 130 can be mounted on or embedded in the haptics 112 (as shown in FIG. 4B), in the lens 111 of the IOL device 110, or in another part of the IOL device 110. Moreover, the controller 130 can receive a detection output from a sensor; the detection output can be related or correspond to the vergence rotation between the subject's eyes. At least partially based on the received detection output, the controller 130 can switch the lens 111 to a suitable or predetermined focal length.

For example, the controller 130 can be operably coupled to and can receive a detection output from a sensor 140 that can be positioned on or embedded in one or more portions of the IOL device 110. For example, the sensor 140 can be mounted on or embedded in the haptics 112 (as shown in FIG. 4B) or in the lens 111 of the IOL device 110. Generally, the sensor 140 can be any suitable sensor for detecting changes in the identifiable field, which can correspond to vergence rotation of the eyes, as described below in more detail.

In an embodiment, the identifiable field can be an identifiable magnetic field. Hence, for example, the sensor 140 can be a magnetic field sensor. Generally, the sensor 140 can be any suitable sensor or multiple sensors, which can be sufficiently miniaturized and can be configured for placement in the subject's eye (e.g., MEMS-based sensors that can be embedded in or mounted on one or more portions of the IOL device 110). Examples of suitable sensors include Hall effect sensors, magnetoresistance sensors (e.g., AMR magnetometer, GMR magnetometer), induction coils, magneto-diodes, Lorentz force based sensors, an electron tunneling based sensor, or a MEMS compass. For example, the sensor 140 can generate a detection output (e.g., a measurable change in voltage or resonant frequency) that can be related to or based on the changes in the position of an identifiable magnetic field, which can be related to the change in vergence between the subject's eyes. In an embodiment, the sensor 140 can generate a signal that can include detection output of the sensor 140.

In an embodiment, the IOL device 110 can include a field source 150 (e.g., a magnetic field source), which can establish an identifiable magnetic field that can be detectable by an additional sensor that can be operably coupled to an additional controller. The field source 150 can be a dipole magnet (e.g., a permanent magnet, an electromagnet, or combination of the foregoing) and can establish or generate a corresponding identifiable dipole magnetic field. Furthermore, the field source 150 can be mounted on or embedded in the IOL device 110. For example, the field source 150 can be embedded in the haptics 112 (as shown in FIG. 4B) or in the lens 111 of the IOL device 110.

In an embodiment, the field source 150 can be generally fixed in or stationary relative to the eye. Additionally or alternatively, the field source 150 can have a predetermine orientation relative to the eye or to the optical axis thereof. For example, the field source can be embedded within the IOL device 110 at a first predetermined orientation relative to the IOL device 110, and the IOL device 110 can be implanted within the eye at a second predetermined orientation relative to the eye. As such, for example, the identifiable field, such as an identifiable magnetic field can have a predetermined orientation relative to the eye or relative to the optical axis thereof.

Moreover, in an embodiment, the IOL device 110 can be positioned in the eye in a manner that movement of the eye results in a corresponding movement of the IOL device 110. Hence, for example, movement of the eye can produce a corresponding movement of the field source 150 and of the magnetic field established thereby. As such, a sensor detects the change in the established identifiable magnetic field, which can correspond to the movement of the identifiable magnetic field and of the eye (e.g., the movement of the eye can be tilting or pivoting of the eye that at least partially corresponds to a vergence rotation between the eyes).

The IOL device(s) can be located in one or in both eyes of the subject. In an embodiment, an IOL device in the first eye can communicate with another IOL in the second eye, and vice versa (e.g., the IOL devices can be operably coupled together). For example, the IOL device in the second eye can send to the IOL device 110 in the first eye the detection output received from a first sensor in the IOL in the second eye, can send focal length determination, etc. In an embodiment, the IOL device 110 can include a communication device 160 (e.g., the controller 130 can be operably coupled to the communication device 160). The communication device 160 can be mounted on or embedded in the IOL device 110. For example, the communication device 160 can be embedded in the haptics 112 (as shown in FIG. 4B) or in the lens 111 of the IOL device 110.

The communication device 160 can be wireless (e.g., the communication device 160 can be a transmitter or a transceiver) or wired. For example, a wireless (e.g., RF-based or US-based) connection can be established between the communication device 160 and another or additional communication device. Alternatively, the communication device 160 and another communication device can have a wired connection therebetween. For example, an electrical conductor connecting the communication device 160 and another communication device can be implanted in or near the eyes of the subject. In any embodiment, the communication device 160 can be operably coupled to the additional communication device, such as to send data therebetween.

In an embodiment, the controller 130, sensor 140, field source 150, or communication device 160 can be operably coupled or connected to a power source. For example, the power source can include a rechargeable energy storage device or battery (not shown) that can be mounted on or embedded in the IOL device 110. The battery can be wirelessly recharged (e.g., a wireless or inductive charger can recharge the battery). In an embodiment, the battery can be operably connected to a photovoltaic cell that can be mounted on or embedded in the IOL device 110. Alternatively or additionally, the battery can be operably connected or coupled to a charge port that can be configured to accept a charging device. In any event, the power source can power one or more of the controller 130, sensor 140, field source 150, or communication device 160.

In an embodiment, the power source can include a parasitic power device, such as an induction coil, one or more photocells, thermoelectric device, or any other device configured to harvest energy from a subject or the environment. For example, the induction coil can include a channel having a magnet therein, the channel passing the induction coil upon movement of the subject (e.g., eye-movement or blinking). In an embodiment, an induction coil can be disposed in the eye of a subject (e.g., in or adjacent to the IOL) and a corresponding magnet can be positioned on an adjacent part of the subject (e.g., an eyelid or bridge of the nose) whereby movement of the eye or eyelid can cause a current in the induction coil.

Again, while the IOL device 110 is described as including the controller 130, sensor 140, field source 150, and communication device 160, configurations of the IOL device 110 can vary from one embodiment to the next. In particular, for example, the IOL device 110 can include only the controller 130 and sensor 140, and the sensor 140 can detect a change in the identifiable field (e.g., identifiable magnetic field) established by the field source positioned externally to the IOL device 110 or to the eye in which the IOL device 110 is located (e.g., the field source can be located in another eye, can be implanted near the eyes, such as on a nose, can be wearable, etc.). In an embodiment, the IOL device 110 can include only the field source 150, and as the eye together with the IOL device 110 tilt or pivot, a sensor in the second eye can detect the change in the identifiable magnetic field that is established by the field source 150 (e.g., another IOL device in the second eye can include a sensor operably coupled to a controller).

As described above, the IOL system can include a single IOL device or multiple IOL devices (e.g., an IOL device can be located in one or in both eyes of the subject). Generally, the IOL devices of the IOL system can be similar to or the same as the IOL device 110. It should be appreciated, however, that any of the IOL devices included in the IOL systems described herein can include or can be operably coupled to any number of controllers, sensors, field sources, communication devices, or combinations thereof, which can be similar to or the same as the controller 130, sensor 140, field source 150, and communication device 160.

FIGS. 5A-5D schematically illustrate an IOL system 100a that includes a first IOL device 110a in the first or right eye (not shown), and a second IOL device 110b in the second or left eye (not shown), according to an embodiment. It should be appreciated that designations, first eye/right eye and second eye/left eye are used for ease of description only and should not be read as limiting (e.g., the first IOL device 110a can be positioned in the second or left eye and the second IOL device 110b can be positioned in the first or right eye). Except as otherwise described herein, the first IOL device 110a, second IOL device 110b, and their elements and components can be similar to or the same as the IOL device 110 (FIGS. 3-4B) and its corresponding elements and components.

Figure 5A:
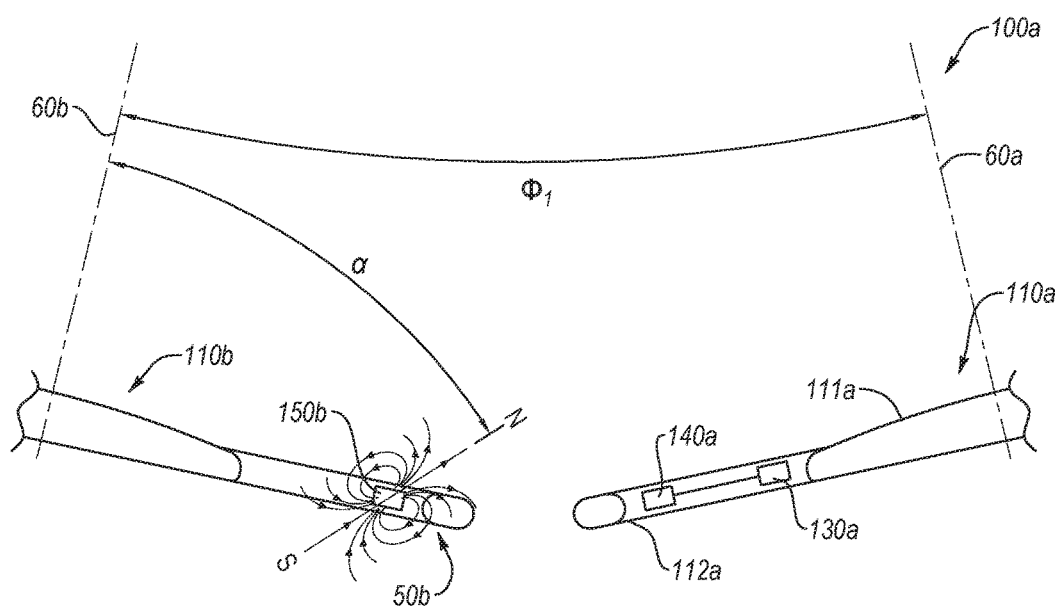
FIG. 5A is a schematic top view of an IOL system that includes two IOL devices oriented by the subject's eyes at a first vergence therebetween according to an embodiment.

FIG. 5A illustrates the first IOL device 110a and the second IOL device 110b, with respective first and second optical axes 60a and 60b of the first and second eyes oriented to define a first angle $\phi_1$ therebetween, at which the eyes are focused on first object at first distance from the subject. In an embodiment, the first IOL device 110a includes a sensor 140a operably coupled to a controller 130a including control electrical circuitry (e.g., the sensor 140a or controller 130a can be embedded in the first IOL device 110a, such as in the haptics 112a of the first IOL device 110a). Moreover, the controller 130a can be operably coupled to first lens 111a of the first IOL device 110a, such as to switch or direct switch of the focal length of the first lens 111a at least between to different focal lengths.

In an embodiment, the second IOL device 110b can include a magnetic field source 50b mounted thereon or embedded therein. The magnetic field source 150b can establish an identifiable magnetic field 50b that can be sensed by the sensor 140a. More specifically, for example, the sensor 140a can detect the change in orientation or location of the identifiable magnetic field 50b. It should be also appreciated that the magnetic field source 50*b* can be positioned or secured in the subject's second eye without the second IOL device 110*b* (e.g., the magnetic field source 50*b* can be implanted in the eye, such as in the sclera of the eye). In any event, in one or more embodiments, the magnetic field source 150*b* can move and tilt together with the second eye (correspondingly moving the identifiable magnetic field 50*b*), and the sensor 140*a* can detect the change in the orientation or location of the identifiable magnetic field 50*b*. It should be also appreciated that any of the elements or components described herein as included in one or more IOL devices can be directly implanted in the eye, without implanting an IOL device in that eye (e.g., a second, a controller, etc., can be implanted in the eye).

In an embodiment, the controller 130*a* is configured to correlate the detected change in the identifiable magnetic field 50*b* with the vergence rotation between the eyes. For example, the sensor 140*a* can generate a detection output that can correspond to a change at least partially corresponding to the vergence rotation by detecting a changed component of the identifiable magnetic field, which can be in a direction substantially perpendicular to a direction of a dominant component of the identifiable magnetic field. Furthermore, the detection output can be received by the controller 130*a*, and based on the detection output, the controller 130*a* can determine the vergence rotation between the eyes.

In an embodiment, at least partially based on or from the vergence rotation, the controller 130*a* can determine an apparent object distance (e.g., the distance from the subject to the object on which the subject's eyes are attempting to focus). In an embodiment, at least partially based on the determined distance, the controller 130*a* can determine the first or second focal length for the switchable lens (e.g., for the switchable lens 111*a* or for the switchable lens of the second IOL 110*b*) and can switch or direct switch of the switchable lens to the determined focal length.

Generally, the magnetic field source 50*b* can be any suitable magnet, which can establish any suitable magnetic field that can vary from one embodiment to the next. In the illustrated embodiment, the magnetic field source 50*b* is a dipole magnet, such as a permanent magnet (e.g., a ferromagnet). In an embodiment, the magnetic field source 50*b* can be a dipole electromagnet. In an embodiment, the magnetic field source 50*b* can generate a magnetic field having both a dipole and a non-dipole contribution. In such an embodiment, the non-dipole contributions generally weaken more with distance from the magnetic field source 50*b* than do the dipole contributions so that at a sufficient distance from the magnetic field source 50*b* (e.g., at the sensor location 140*a*), the dominant contribution is that of a magnetic dipole. In an embodiment, the electromagnet can be operably coupled to the controller 130*a* or to an additional controller (e.g., to a controller in the second IOL device 110*b*), which can turn on or off the electromagnet or can change an intensity of the magnetic field established or generated thereby. For example, the electromagnet can be pulsed in a manner that can distinguish or identify the magnetic field established thereby from other, interfering magnetic fields that can be present in the subject's environment. Moreover, based on the detection output from the sensor 140*a*, the controller 130*a* can distinguish the identifiable pulsed magnetic field from other magnetic fields.

Generally, as mentioned above, the sensor 140*a* can be any suitable sensor or multiple sensors, which can be sufficiently miniaturized for placement in the subject's eye (e.g., MEMS based sensors that can be embedded in or mounted on the first IOL device 110*a*). Examples of suitable sensors include Hall effect sensors, magnetoresistance sensors (e.g., AMR magnetometer, GMR magnetometer), induction coils, magneto-diodes, Lorentz force based sensors, Electron Tunneling based sensor, MEMS compass, etc. In any event, the sensor 140*a* can be or can include any suitable sensor or combination of sensors that can detect the change in the location or orientation of the identifiable magnetic field 50*b*.

In an embodiment, the first IOL device 110*a* can be positioned at a predetermined location or orientation relative to the first optical axis 60*a* of the first eye, and the second IOL device 110*b* or the identifiable magnetic field 50*b* or pole axis of the magnetic field source 50*b* or the identifiable magnetic field 50*b* can be oriented relative to the second optical axis 60*b* of the second eye at a predetermined pitch angle α. Generally, the predetermined pitch angle can be any suitable angle, which can vary from one embodiment to the next. For example, the pitch angle α can be a non-parallel angle relative to the first or second optical axes 60*a* or 60*b*, an obtuse angle, or an acute angle. Moreover, as described below in more detail, the pitch angle can be 0°, such that a magnetic field component of the identifiable magnetic field 50*b* is substantially parallel to the second optical axis 60*b*.

Furthermore, the identifiable magnetic field 50*b* can be oriented such that the sensor 140*a* or the controller 130*a* can distinguish between in-tilt or convergence of the eyes (e.g., when the subject attempts to change focus on from a first object to a second object that is closer to the subject) from co-tilt of the eyes (e.g., when the subject tilts or pivots eyes to focus on an object located peripherally, such as to the left or to the right of the subject). For example, the identifiable magnetic field 50*b* can be oriented at about 45° relative to the second optical axis 60*b* (e.g., within less than 1° of the 45°, within less than 2° of the 45°, within less than 5° of the 45°).

It should be appreciated that the identifiable magnetic field 50*b* can have any suitable orientation relative to the second optical axis 60*b*. For example, the identifiable magnetic field 50*b* can be oriented relative to the second optical axis 60*b* such that convergence of the eyes results in an increased magnitude or changed direction of the magnetic field vector (e.g., Lorentz force vector), which can be distinguishable from the direction of the magnetic field vector sensed by the sensor 140*a* when the eyes co-tilt, as discussed below in more detail. In other words, the identifiable magnetic field 50*b* can be oriented such that the detection output received from the sensor 140*a* can be processed by the controller 130*a* to distinguish or identify the change in magnitude or direction of the Lorentz force vector of the identifiable magnetic field 50*b* in a manner that the controller 130*a* can distinguish convergence or in-tilt of the eyes from co-tilt.

It should be also appreciated that the sensor 140*a* of the first IOL device 110*a* can be configured to measure the strength and direction of the magnetic field, to measure the component of the magnetic field in a specific sensitivity direction, or to include multiple (collocated or not) magnetic sensors each of which is configured to measure separately directed components of the magnetic field. In an embodiment, the sensor 140*a* includes a sensor configured to measure a magnetic field component oriented at 0° relative to the first optical axis 60*a*. In an embodiment, the sensor 140*a* includes a sensor configured to measure a magnetic field component oriented at 90° relative to the first optical axis 60*a* (e.g., in the plane of the first IOL device 110*a*) directed to or away from the second IOL device 110*b*. The sensor 140*a* is mounted or embedded within the first IOL device 110*a* so that as the first eye tilts, changing the direction of first optical axis 60*a* and first IOL device 110*a*, the sensitivity direction of the sensor 140*a* also changes. Accordingly, the value of a specific directional component of magnetic field measured by the sensor 140*a* will change based on changes in the tilt of the first eye. It should be further appreciated, that the value of a specific directional component of magnetic field measured by the sensor 140*a* will also be changed by changes in the direction the magnetic field source 50*b*, and the accompanying changes in the field at the location of the sensor 140*a*. Since the magnetic field source 50*b* is implanted in the second eye (either directly, or indirectly via being mounted in the second IOL device 110*b*), then field values measured by the sensor 140*a* will change based on changes in the tilt of the second eye. Accordingly, field values measured by the sensor 140*a* will change based on changes in the tilt of both the first eye and the second eye.

It should be also appreciated that the second IOL device 110*b* can include multiple magnets that can establish multiple identifiable magnetic fields. Moreover, a single identifiable magnetic field oriented at an acute or obtuse angle relative to the second optic axis 60*b* can be represented by superpositioning two or more identifiable magnetic fields established by multiple magnets. Conversely, a single tilted identifiable magnetic field source (e.g., magnetic field source oriented at 45° relative to the second optic axis 60*b*) can be represented as two magnetic field sources: e.g., an in-plane field source $m_\|$ oriented parallel to the plane of the IOL (i.e., orthogonal to the optical axis 60*b*), and an out-of-plane field source $m_\perp$ oriented perpendicular to the plane of the IOL (i.e., along the optical axis 60*b*). The sensor 140*a* can be configured to measure magnetic field at a specified angle relative to the optical axis 60*a*. In an embodiment, one or more sensors 140*a* can measure an in-plane magnetic field component $b_\|$ and an out-of-plane magnetic field component $b_\perp$. For dipole-dominated magnetic fields, the relative magnetic field components measured by sensor 140*a* can be written in matrix form as $$\begin{pmatrix} b_\perp \\ b_\| \end{pmatrix} = \begin{pmatrix} B_{\perp\perp} & B_{\perp\|} \\ B_{\|\perp} & B_{\|\|} \end{pmatrix} \begin{pmatrix} m_\perp \\ m_\| \end{pmatrix}$$

For a magnetic field generated by a dipole source, the dimensionless field b at a given distance depends on the orientation of the source, $\hat{m}$, and that of the location $\hat{r}$ at which the field is being measured:

$$b = 3(\hat{m} \cdot \hat{r})\hat{r} - \hat{m}$$

In this case, the four matrix elements are (using $\theta_1$ as the tilt of the first eye and $\theta_2$ for the second eye):

$$B_{\perp\perp} = 2 \sin\theta_1 \sin\theta_2 - \cos\theta_1 \cos\theta_2$$

$$B_{\perp\|} = 2 \sin\theta_1 \cos\theta_2 + \cos\theta_1 \sin\theta_2$$

$$B_{\|\perp} = 2 \cos\theta_1 \sin\theta_2 + \sin\theta_1 \cos\theta_2$$

$$B_{\|\|} = 2 \cos\theta_1 \cos\theta_2 - \sin\theta_1 \sin\theta_2$$

Since eye rotations are small, we can usefully approximate these relations as:

$$B_{\perp\perp} = -1$$

$$B_{\perp\|} = 2\theta_1 + \theta_2$$

$$B_{\|\perp} = 2\theta_2 + \theta_1$$

$$B_{\|\|} = 2$$

The dominant matrix elements; $B_{\perp\perp}$, the perpendicular field due to a perpendicular source and $B_{\|\|}$, the parallel field due to a parallel source are not sensitive to eye tilts. However, the cross terms, $B_{\perp\|}$, the perpendicular field due to a parallel source and $B_{\|\perp}$, the parallel field due to a perpendicular source are sensitive to eye tilts, depending on both of them. Neither one of these elements, by itself, is capable of distinguishing between vergence and co-tilt, but in combination, they are.

Vergence: $\phi = \theta_2 - \theta_1 = B_{\|\perp} - B_{\perp\|}$

Co-Tilt: $\psi = \frac{1}{2}(\theta_1 + \theta_2) = \frac{1}{6}(B_{\|\perp} + B_{\perp\|})$ In an embodiment, the magnetic field source 50*b* in the second eye includes two magnetic field sources, one with dipole moment $m_\perp$ oriented perpendicular to the plane of the second IOL (i.e., along the optical axis 60*b*), and the other with dipole moment $m_\|$ oriented parallel to the plane of the IOL (i.e., orthogonal to the optical axis 60*b*). In such an embodiment, the sensor 140*a* in the first eye is configured to measure magnetic fields in two orthogonal directions, measuring an in-plane magnetic field component $b_\|$ and an out-of-plane magnetic field component $b_\perp$. As described above, in this embodiment, the cross terms $B_{\perp\|}$ and $B_{\|\perp}$ can be determined, and used to determine the vergence between the two eyes; if desired, these can also determine the co-tilt. In some situations (e.g., when magnetic dipole moments $m_\perp$ and $m_\|$ are produced with permanent magnets), the measured field component $b_\|$ may include contributions from both $m_\perp$ and $m_\|$, likewise for $b_\perp$. In such situations, the controller can separate these contributions (e.g., distinguish $B_{\|\|}$ from $B_{\|\perp}$, and distinguish $B_{\perp\|}$ from $B_{\perp\perp}$) by using the fact that $B_{\|\|}$ and $B_{\perp\perp}$ are insensitive to eye tilts (and hence will remain substantially constant in time); changes in measured $b_\|$ or $b_\perp$ values correspond to the $B_{\|\perp}$ and $B_{\perp\|}$ terms. In other embodiments, such potential ambiguities can be avoided by use of time variable magnetic field sources (e.g., pulsed electromagnets), such that $m_\perp$ and $m_\|$ are active at different times.

In another embodiment, the magnetic field source 50*b* in the second eye can be tilted at an angle $\alpha$ from the optical axis 60*b*. In this embodiment, the sensor 140*a* can be configured to measure the magnetic field component along a direction generally perpendicular to the magnetic field source 60*b*, i.e., at an angle ($\alpha - 90°$) from optical axis 60*a*, pointing back towards the second eye. In this situation, the proportionality B between the detected field and the dipole source is:

$$B = -0.5 \sin\phi - 1.5 \sin 2\alpha \cos\phi - 1.5 \cos 2\alpha \sin 2\psi$$

In general, this depends upon both the vergence $\phi$ and the co-tilt $\psi$. However, by properly selecting the tilt angle $\alpha$ to be 45 degrees, the detected signal no longer depends on co-tilt, and can be directly used to determine vergence.

$$B = -0.5 \sin\phi - 1.5 \cos\phi \approx -1.5 - 0.5\phi$$

The controller 130*a* including the control electrical circuitry thereof can distinguish between co-tilt and in-tilt (vergence) using the above methodology and formulas. It is apparent that a similar arrangement of components (i.e., magnetic field source 50*a* in the first eye and sensor 140*b* in the second eye) can be employed to enable a controller 130*b* (located for example in the second eye) to independently determine vergence and/or co-tilt. It is also apparent that, for the above embodiment with field source and sensor oriented at 45° from the optical axes, the magnetic field source 50*a* can be oriented perpendicular to the sensitivity direction of sensor 140*a*, while the sensitivity direction of sensor 140*b* can be oriented perpendicular to magnetic field source 50*b*; such alignments may be advantageous for signal to noise purposes.

As described above, components of the first IOL device 110*a* can be oriented at a predetermined angle relative to an optical axis 60*a* of the first eye. For example, the sensor 140*a* can be positioned such that when the eyes converge (e.g., in a manner representative of the eyes changing focus to a closer object), the sensor 140*a* pivots with the eye to be more sensitive to the identifiable magnetic field 50*b* (as compared before eye movement); when the eyes co-tilt in a first direction (e.g., in a manner representative of the eyes looking to the left (as shown in FIG. 5C)), the sensor 140*a* moves together with the eye and can be aligned closer and be more sensitive to the second, south pole of the identifiable magnetic field 50*b* than to the north pole; when the eyes co-tilt in a second direction (e.g., in a manner representative of the eyes looking to the right), the sensor 140*a* can move with the eye and can be aligned closer to and be more sensitive to the north pole of the identifiable magnetic field 50*b* (as compared before eye movement (as shown in FIG. 5D)).

In any event, in an embodiment, when the controller 130*a* receives the detection output generated by the sensor 140*a*, the controller 130*a* can identify vergence rotation between the eyes (e.g., convergence) and can distinguish the vergence rotation from co-tilt of the eyes. Moreover, the controller 130*a* can direct the first IOL device 110*a* to change the focal length from the first focal length to the second focal length at least partially based on the detection output(s) of the sensor 140*a*, which can correspond to vergence rotation between the eyes.

As mentioned above, in the illustrated embodiment, the magnetic field source 150*b* can be included in the second IOL device 110*b* that can be located in the subject's second eye. For example, the second IOL device 110*b* can include a second lens 111*b* that can be similar to or the same as the first lens 111*a* of the first IOL device 110*a*. In an embodiment, the second IOL device 110*b* also can include an additional or second controller (not shown) that can switch or direct switching of the second IOL device 110*b* between two or more focal lengths. Moreover, the controller 130*a* can communicate with the second controller and can send the focal length indication thereto. For example, the controller 130*a* can be operably connected to a first communication device (not shown), and the second controller can be connected to a second communication device (not shown) that can be in communication with or configured to communicate with the first communication device. In other words, the first and second communication devices can be operably coupled.

For example, via communication between the first and second communication devices, the controller 130*a* can send to the additional, second controller the controller data. Generally, controller data can include any data or any number of suitable parameters. In an embodiment, the controller data can include information or instructions for switching the first lens 111*a* or the second lens 111*b* to the first focal length or to the second focal length (e.g., the controller data can associated with selected focal length for the first lens 111*a* or for the second lens 111*b*). Additionally or alternatively, the controller data can include or can be associated with the detection output of the sensor 140*a*.

In an embodiment, the first IOL device 110*a* or the second IOL device 110*b* can include additional or alternative sensors that can detect eye movement in a manner that can aid the controller 130*a* or the additional, second controller to identify or determine vergence rotation between the eyes. For example, the first IOL device 110*a* or second IOL device 110*b* can include one or more accelerometers or gyroscopes. More specifically, outputs generated by the accelerometers or gyroscopes can indicate the direction of rotation or tilting for the first or second eyes.

In an embodiment, the direction of tilting or rotation detected or sensed by the accelerometers or gyroscopes in the first eye can be communicated to and compared with the direction of tilting or rotation detected or sensed by the accelerometers or gyroscopes in the second eye. For example, the controller 130*a* can communicate with the additional, second controller (as described above) and can send controller data thereto (e.g., the controller data can include processed or unprocessed output from the accelerometers or from the gyroscopes). The controller 130*a* or the additional, second controller can distinguish co-tilting or the eyes are tilting in the same direction from vergence rotation or the eyes are tilting in different directions (e.g., to focus on an object closer or farther away from previously viewed object). Moreover, based at least partially on the outputs received from the accelerometers or gyroscopes in the first and second eyes, the controller 130*a* or the additional, second controller can determine the focal lengths for the first lens 111*a* or for the second lens 111*b*.

In an embodiment, the controller 130*a* or the second controller can use the detection outputs from the accelerometers or gyroscopes to cross-check or verify the determination on the change in vergence between the eyes, which can be based on the output from the sensor 140*a*. Conversely, the controller 130*a* or the second controller can use the detection outputs from the sensor 140*a* to cross-check or compare the determination or identification of the vergence rotation between the eyes, which can be based on the output from the accelerometers or gyroscopes. Moreover, in an embodiment, the accelerometers or gyroscopes can be initially or periodically calibrated (e.g., based on the detection outputs from the sensor 140*a*) to adjust for noise, drift, other errors, etc.

Figure 5B:
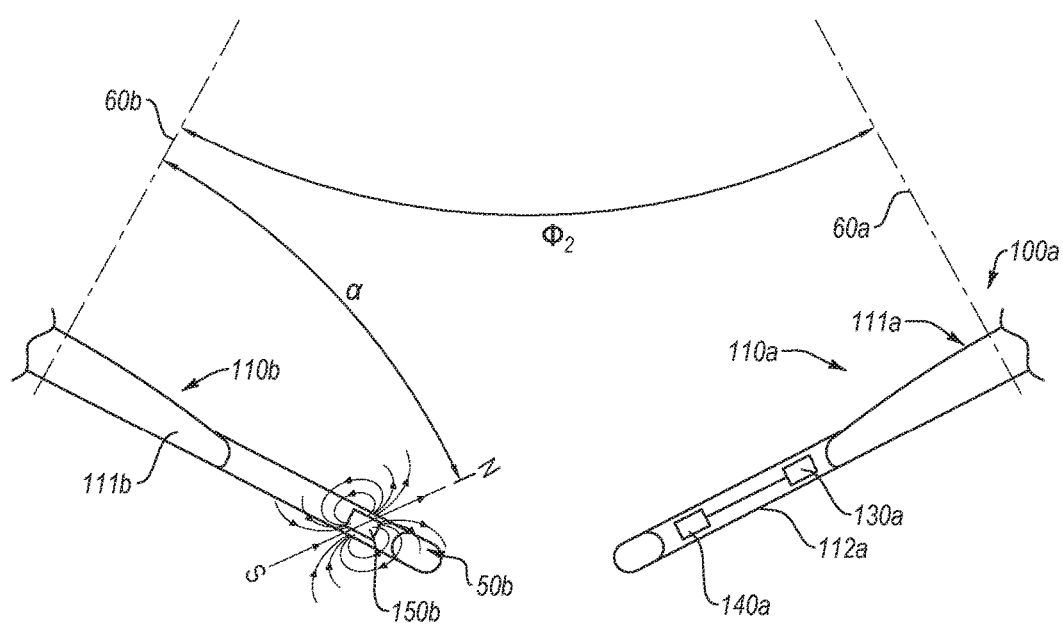
FIG. 5B is a schematic top view of the IOL system of FIG. 5A in which the IOL devices are oriented by the subject's eyes at a second vergence therebetween according to an embodiment.
Figure 5C:
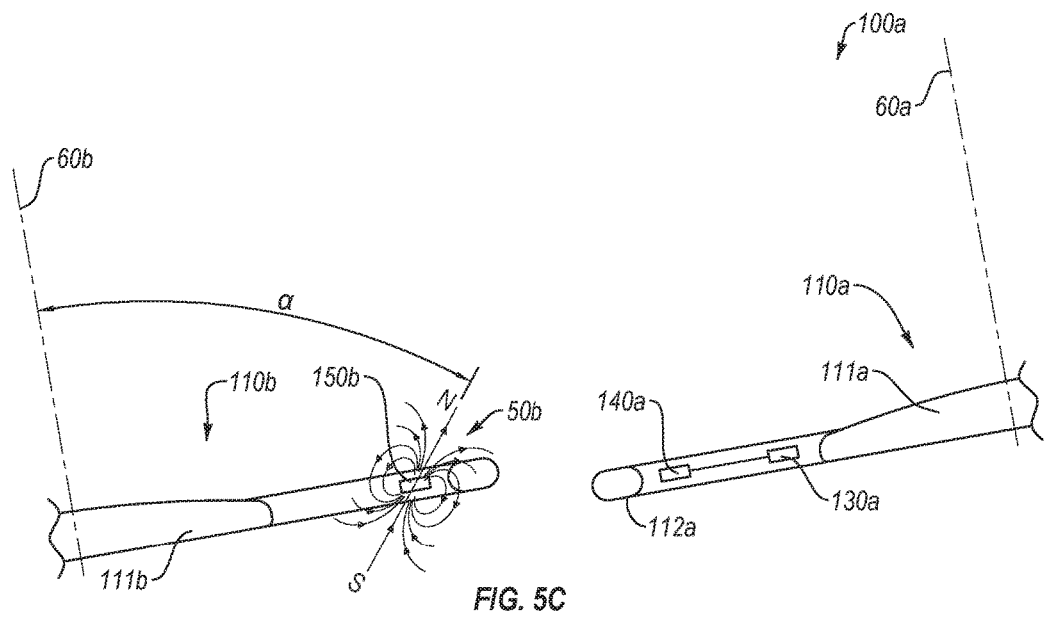
FIG. 5C is a schematic top view of the IOL system of FIG. 5A in which the IOL devices are oriented by the subject's eyes co-tilted in a first direction according to an embodiment.
Figure 5D:
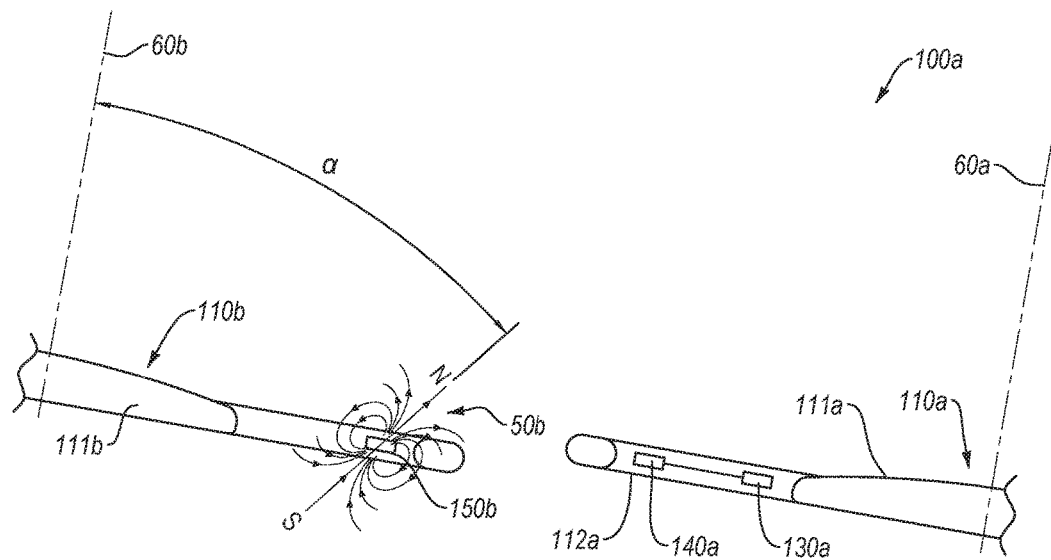
FIG. 5D is a schematic top view of the IOL system of FIG. 5A in which the IOL devices are oriented by the subject's eyes co-tilted in a second direction according to an embodiment.

FIG. 5B shows the first IOL device 110*a* and second IOL device 110*b* and corresponding eyes (not shown) tilted compared with the respective orientations thereof shown in FIG. 5A responsive to corresponding convergence of the first and second eyes of the subject. In particular, for example, the first IOL device 110*a* can remain substantially stationary relative to first optical axis 60*a*, and the second IOL device 110*b* can remain substantially stationary relative to the second optical axis 60*b*. Hence, as the first eye tilts toward or away from the second eye, the first IOL device 110*a* can correspondingly tilt toward the second IOL device 110*b* (e.g., vergence rotation between the first and second eyes can produce a corresponding change in relative orientations or positions of the first IOL device 110*a* and second IOL device 110*b*). In particular, the first and second eyes can converge to form the second angle $\phi_2$ between the respective first and second optical axes 60*a*, 60*b* thereof, and the first IOL device 110*a* and second IOL device 110*b* can correspondingly converge together.

As described above, for example, when the first IOL device 110*a* and second IOL device 110*b* converge, the sensor 140*a* can be reoriented or repositioned relative to the magnetic field source 150*b* and relative to the identifiable magnetic field 50*b* established thereby. More specifically, for example, the identifiable magnetic field 50b and the sensor 140a can be reoriented relative to each other such that the sensor 140a can generate an output related to a change in the direction of the magnetic field vector or magnitude thereof. Furthermore, at least partially based on the output from the sensor 140a, the controller 130a can distinguish vergence rotation between the eyes (e.g., convergence of the eyes) from co-tilt of the eyes, as described above.

Furthermore, as shown in FIG. 5C, when the eyes tilt in the same direction or co-tilt towards the left, such that the respective first and second optical axes 60a, 60b thereof are generally parallel to each other, while the first IOL device 110a and the second IOL device 110b remain generally parallel to one another, the angular position of sensor 140a relative to the polar axis of magnetic field source 50b changes. The sensor 140a and the identifiable magnetic field 50b are reoriented, such that the relative position of the sensor 140a changes from being closer to the north pole of the identifiable magnetic field 50b to being closer to the south pole of the identifiable magnetic field 50b. Hence, for example, the detection output from the sensor 140a can correspond to a detected change in the direction of the magnetic field vector, and the controller 130a can correlate the detection output from the sensor 140a to the co-tilt of the eyes.

Alternatively, as shown in FIG. 5D, the eyes can co-tilt towards the right, such that while the first IOL device 110a and the second IOL device 110b remain generally parallel to one another, the angular position of sensor 140a relative to the polar axis of magnetic field source 50b changes. For example, after repositioning or reorientation of the sensor 140a and of the identifiable magnetic field 50b (responsive to co-tilt of the eyes to the right), the detection output from the sensor 140a can correspond to a detected change in the magnetic field vector, and the controller 130a can correlate the detection output from the sensor 140a to the co-tilt of the eyes. In any event, the first IOL device 110a and second IOL device 110b can be positioned or oriented relative to the first optical axis 60a and second optical axis 60b such that the detection output from the sensor 140a can be correlated by the controller 130a to distinguish vergence rotation (e.g., convergence or in-tilt of the eyes) from the co-tilt of the eyes.

Figure 6A:
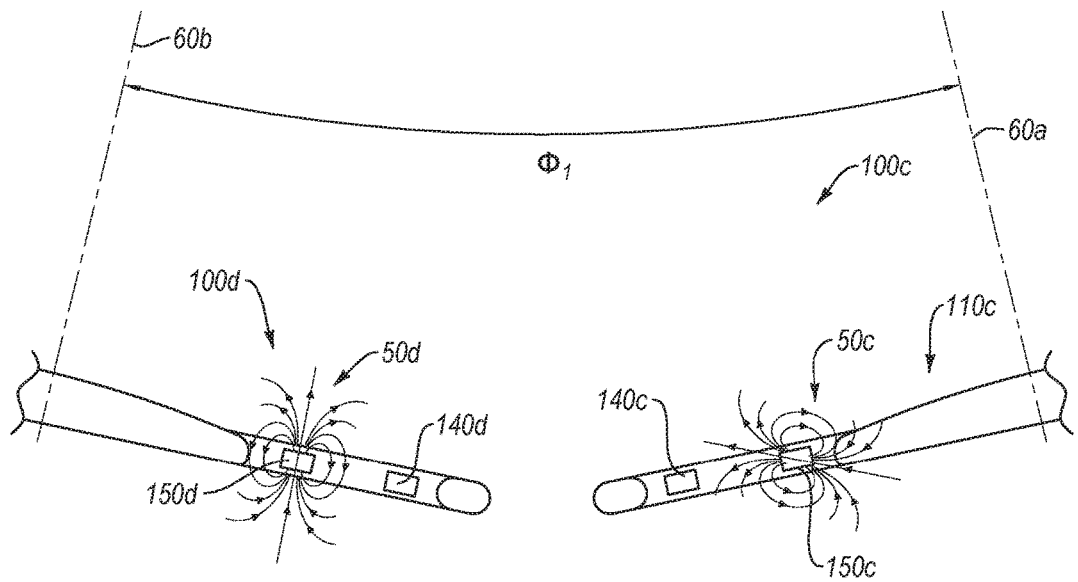
FIG. 6A is a schematic top view of an IOL system that includes two IOL devices oriented by the subject's eyes at a first vergence therebetween according to another embodiment.
Figure 6B:
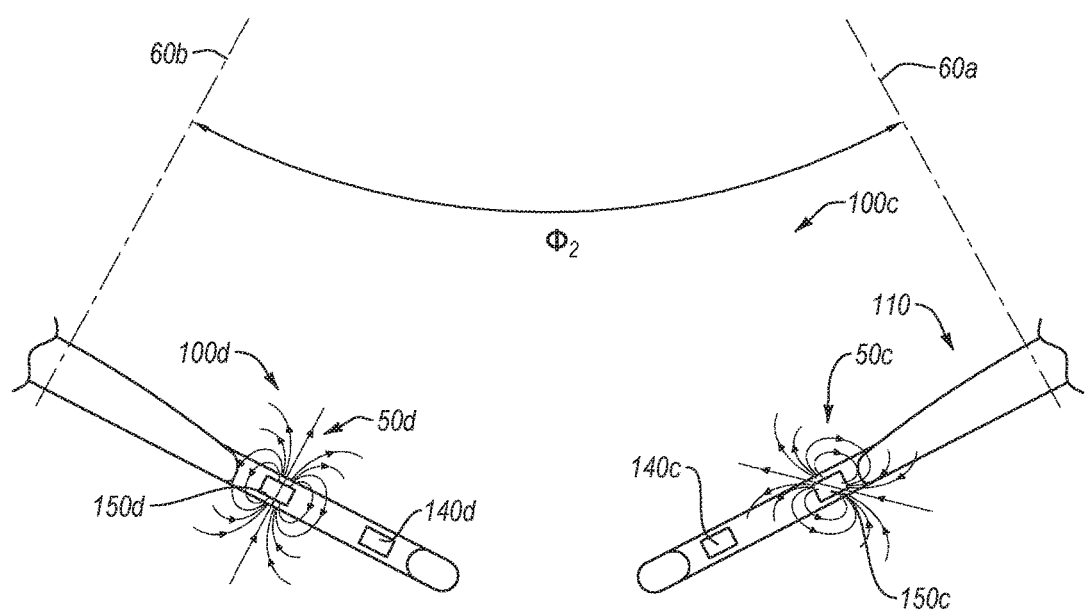
FIG. 6B is a schematic top view of the IOL system of FIG. 6A in which the IOL devices are oriented by the subject's eyes at a second vergence therebetween according to an embodiment.

As described above, the IOL system can include multiple identifiable fields and multiple corresponding sensors that can detect relative change in position or orientation therebetween. FIGS. 6A and 6B illustrate an IOL system 100c that includes a first IOL device 110c and a second IOL device 110d and establishes multiple identifiable magnetic fields, according to an embodiment. In particular, FIG. 6A illustrates the first IOL device 110c and the second IOL device 110d at first respective locations or orientations relative to each other when the subject's eyes (not shown) focus or attempt to focus at a first focal length, such that the respective first and second optical axes 60a, 60b of the first and second eye define the first angle $\phi_1$ therebetween. For example, the first IOL device 110c and the second IOL device 110d can be substantially fixed relative to the first and second optical axes 60a, 60b of the subject's eyes. FIG. 6B illustrates the first IOL device 110c and the second IOL device 110d at second respective locations or orientations relative to each other when the subject is attempting to focus or focusing the eyes (not shown) at a second focal length, such that the first optical axis the 60a and second optical axis 60b define the second angle $\phi_2$ therebetween. The following describes the IOL system 100c as the subject in-tilts and out-tilts the eyes (e.g., such that vergence rotation between the eyes tilts or pivots the first and second optical axis the 60a, 60b between defining first angle $\phi_1$ and second angle $\phi_2$).

Except as otherwise described herein, the IOL system 100c and its elements and components can be similar to or the same as any of the IOL systems 100, 100a (FIGS. 1-5D) and their corresponding elements and components. For example, the first IOL device 110c can include a first sensor 140c and a first controller (not shown) including control electrical circuitry, which can be similar to or the same as the sensor 140a and controller 130a of the first IOL device 110a (FIGS. 5A-5D). Similarly, the second IOL device 110d can include a second sensor 140d and a second controller (not shown) including control electrical circuitry, which also can be similar to or the same as the sensor 140a and controller 130a of the first IOL device 110a (FIGS. 5A-5D).

In the illustrated embodiment, the first IOL device 110c includes a first field source 150c that can establish a first identifiable magnetic field 50c, and the second IOL device 110d includes a second field source 150d that can establish a second identifiable magnetic field 50d. Generally, the first identifiable magnetic field 50c and second identifiable magnetic field 50d can have any suitable orientation relative to the first optical axis 60a or to the second optical axis 60b of the first eye and second eye. In an embodiment, the first identifiable magnetic field 50c can be oriented at about 90° relative to the first optical axis 60b, and the second identifiable magnetic field 50d can be oriented generally parallel to the second optical axis 60b, or vice versa. Moreover, the first identifiable magnetic field 50c and second identifiable magnetic field 50d can have any suitable orientation relative to each other. For example, the first identifiable magnetic field 50c and the second identifiable magnetic field 50d can be oriented generally perpendicular to each other (e.g., when the first and second optical axes 60a, 60b are relatively oriented to define the first angle or the second angle $\phi_2$). In an embodiment, the first identifiable magnetic field 50c or the second identifiable magnetic field 50d can be oriented generally parallel to an axis extending between the eyes.

As described above, the first sensor 140c and second sensor 140d can detect change in the position or orientation of the respective second identifiable magnetic field 50d and first identifiable magnetic field 50c as the eyes together with the first IOL device 110c and second IOL device 110d converge or diverge. For example, the first sensor 140c can sense the first identifiable magnetic field 50d and can generate a first detection output as the second identifiable magnetic field 50d and the first sensor 140c move relative to each other. In an embodiment, the first sensor 140c can detect a changed component of the second identifiable magnetic field 50d (e.g., in a direction that is substantially perpendicular to the dominant component of the second identifiable magnetic field 50d). For example, the first detection output of the first sensor 140c can at least partially correspond to the vergence rotation between the eyes. The second sensor 140d can detect a changed component of the first identifiable magnetic field 50c (e.g., in a direction that is substantially perpendicular to the dominant component of the first identifiable magnetic field 50c), which can at least partially correspond to the vergence rotation between the eyes. As such, a second detection output of the second sensor 140d also can at least partially correspond to a change in the vergence between the eyes or to vergence rotation. As described below in more detail, the first or second controllers can compare the first and second detection outputs to determine the vergence rotation between the eyes.

In one or more embodiments, the first and second controllers can receive the corresponding first and second detection outputs from the respective first and second sensors 140c, 140d and can process the detection outputs to generate controller data based thereon (e.g., can identify or determine vergence rotation between the eyes or can distinguish vergence rotation from co-tilt of the eyes). In an embodiment, the controller data can include the first and second detection outputs. Moreover, the first controller can send the controller data to the second controller (e.g., via corresponding communication devices), or vice versa. Hence, for example, the first or the second controller can receive first and second detection outputs. Furthermore, in an embodiment, the first or second controller can compare the first and second detection outputs to determine the vergence rotation between the eyes (e.g., to distinguish convergence, divergence, and co-tilt of the eyes).

In an embodiment, after determining the vergence rotation between the eyes, the first or second controller can determine the suitable or selectable focal length for the first IOL device 110c or for the second IOL device 110d. For example, as described above, the first IOL device 110c or second IOL device 110d can include one or more switchable lenses that can be switched between two or more focal lengths (e.g., the first or second controllers can switch or direct switching of the switchable lenses). The first controller can direct the first IOL device 110c to switch to a first focal length or to a second focal length based on the determined vergence rotation. Analogously, the second controller can direct the second IOL device 110d to switch to a first focal length or to a second focal length based on the determined vergence rotation. In an embodiment, the first controller can send controller data to the second controller (or vice versa), and the controller data can include the determined vergence rotation or change in the vergence between the eyes or the suitable or selected focal length for the first IOL device 110c or second IOL device 110d.

Figure 7A:
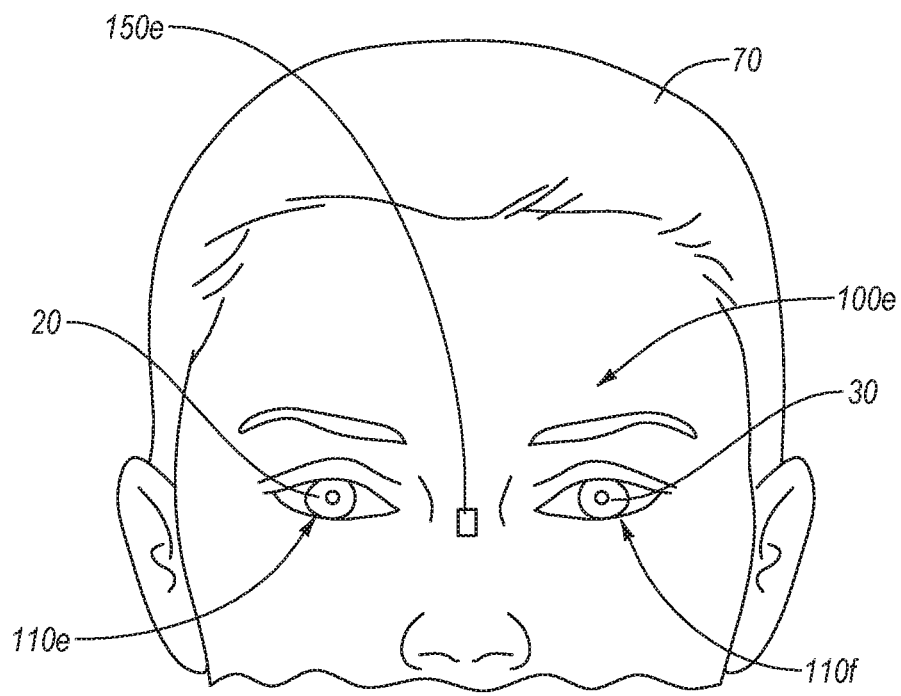
FIG. 7A is a schematic view of an IOL system that includes two IOL devices oriented by the subject's eyes at a first vergence therebetween according to yet another embodiment.
Figure 7B:
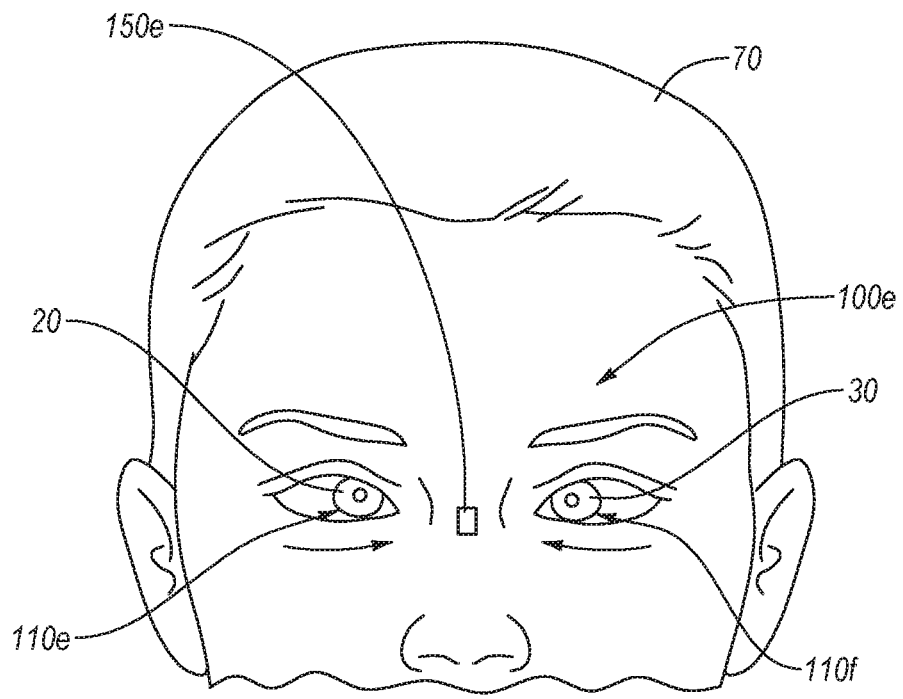
FIG. 7B is a schematic view of the IOL system of FIG. 7A in which the IOL devices are oriented by the subject's eyes at a second vergence therebetween.

As described above, in an embodiment, the IOL system can include a field source positioned externally to the subject's eyes. FIGS. 7A and 7B illustrate an IOL system 100e that includes IOL devices 110e and 110f located in the respective first and second eyes 20, 30 of a subject 70 and a magnetic field source 150e positioned externally to the first and second eyes 20, 30, according to an embodiment. In particular, FIG. 7A illustrates the first and second eyes 20, 30 of the subject 70 at first tilt, positioned to focus on first object located at first distance from the subject 70. FIG. 7B illustrates the first and second eyes 20, 30 at second tilt, positioned to focus on second object located at second distance from the subject 70. The following describes the IOL system 100e as the subject 70 tilts or pivots the first and second eyes 20, 30 between the first and second tilt positions (e.g., the vergence change between the eyes tilts the first and second eyes 20, 30 between the first and second tilt positions).

In an embodiment, the magnetic field source 150e can establish an identifiable magnetic field that can be detected by one or more sensors in the first IOL device 110e or in the second IOL device 110f, as the subject 70 changes tilt of the first and second eyes 20, 30 between the first tilt and the second tilt. Generally, the magnetic field source 150e can establish the identifiable magnetic field at any suitable angle relative to the first/or second eyes 20, 30 or to the optical axes thereof. For example, similar to the IOL system 100a (FIGS. 5A-5D), the magnetic field source 150e can establish the identifiable magnetic field that is oriented at approximately 45° angle relative to the optical axis of the second eye 30 when the first and second eyes 20, 30 are at the first tilt therebetween. In contrast to the IOL system 100a (FIGS. 5A-5D), the magnetic field established by the magnetic field source 150e can remain substantially stationary relative to the subject 70 (e.g., relative to the head of the subject 70). In an embodiment, movement or tilting of the first eye 20 or the second eye 30 can produce a corresponding relative movement or tilting between the magnetic field source 150e and the sensors of the IOL system 100e (e.g., the identifiable magnetic field established by the magnetic field source 150e can remain stationary relative to the head of the subject, and the sensors of the IOL system 100e can move together with the first and second eyes 20, 30, such as during vergence rotation therebetween).

In an embodiment, the first IOL device 110e can include a first sensor. As the first IOL device 110e pivots or tilts together with the first eye 20, the first sensor can detect a changed component of the identifiable magnetic field in a direction that is substantially perpendicular to the direction of the dominant component of the identifiable magnetic field. Furthermore, the second IOL device 110f can include a second sensor. As the second IOL device 110f pivots or tilts together with the second eye 30, the second sensor can detect a changed component of the identifiable magnetic field in a direction that is substantially perpendicular to the direction of the dominant component of the identifiable magnetic field.

As described above, the first IOL device 110e or the second IOL device 110f can include one or more controllers including control electrical circuitry operably coupled to the respective first and second sensors. For example, the first IOL device 110e can include a first controller operably coupled to the first sensor and configured to receive a first detection output therefrom (e.g., the first sensor can generate the first detection output based on the detected change in a component of the identifiable magnetic field). Similarly, the second IOL device 110f can include a second controller operably coupled to the second sensor and configured to receive a second detection output therefrom (e.g., the second sensor can generate the second detection output based on the detected change in a component of the identifiable magnetic field in a similar manner as described above).

In an embodiment, the first controller can be operably coupled to or can be in communication with the second controller. For example, the first controller can be operably coupled to a first communication device and the second controller can be operably coupled to the second communication device, and the first and second communication devices can be configured to transmit data therebetween. Hence, the first controller can send controller data (which can include the detection output from the first sensor or determination of focal length) to the second controller. Additionally or alternatively, the second controller can send controller data (which can include the detection output from the second sensor or determination of focal length) to the first controller. Moreover, the first controller or the second controller is configured to distinguish vergence rotation from co-tilt rotation of the first and second eyes 20, 30 based on the first and second detection outputs.

As described above, the first or second controller also is adapted to determine a suitable or selectable focal length for one or more switchable lenses. For example, the first IOL device 110e can include a first switchable lens that can be switched between two or more focal lengths. Alternatively or additionally, the second IOL device 110f can include a second switchable lens that can be switched between two or more focal lengths. Hence, the first controller or second controller can direct or switch the first switchable lens or second switchable lens based on the first and second detection outputs.

In an embodiment, the IOL system 100e can include multiple magnetic field sources that can generate multiple corresponding identifiable magnetic fields. Generally, each of the multiple magnetic field sources can be oriented relative to the first eye 20 or second eye 30 (e.g., as measured when the first and second eyes 20, 30 are at the first tilt therebetween). Likewise, multiple magnetic field sources can be oriented relative to one another at any number of suitable angles. For example, a first identifiable magnetic field can be oriented at a first predetermined angle relative to the optical axis of the first eye 20, and a second identifiable magnetic field can be oriented at a second predetermined angle relative to the second eye 30 (e.g., when the first and second eyes 20, 30 are at the tilt).

The magnetic field source 150e or additional or alternative magnetic field sources can be generally fixedly positioned relative to the subject 70 with any number of suitable mechanisms or configurations. For example, the magnetic field source 150e can be implanted near the first eye 20 or second eye 30 of the subject 70 (e.g., near or on the bridge of the nose of the subject 70). Additionally or alternatively, the magnetic field source 150e can be removably positioned on or secured to the subject 70 (e.g., with an adhesive, on a wearable object, such as glasses, etc.). In any embodiment, the magnetic field source 150e can be generally stationary relative to the head of the subject 70, such that tilting or pivoting of the first and second eyes 20, 30 can result in relative movement between the first eye 20 and the identifiable magnetic field and between the second eye 30 and identifiable magnetic field.

In another embodiment, the locations of field sources and field sensors described in conjunction with FIGS. 7A-7B, can be generally reversed. In such an embodiment, the IOL system 110e and the IOL system 110f can include implanted or embedded magnetic field sources, while one or more magnetic field sensors can be generally fixedly positioned relative to the subject 70 (e.g., in locations discussed above with reference to 150e). In this embodiment, the orientations of the magnetic fields change as the eyes tilt, resulting in changed values of magnetic field detected by the fixedly positioned sensor(s). A controller (e.g., a controller external to the IOLs) can receive the signals from the field sensor(s) and determine the tilts of one or both eyes. In particular, the controller can compare tilt values from both eyes to thereby determine vergence, and can distinguish vergence from co-tilt. The controller can then be operatively coupled (e.g., by wireless communication) with controllers in each IOL, which then direct focal length changes of their respective IOL optics. In this embodiment, each IOL only needs a communicative receiver, but does not necessarily require a transmitter.

As described above and as would be appreciated in view of the disclosure, MFL systems can include one or more wearable and/or removable elements that can be removed from the subject. Moreover, the wearable and/or removable elements can include any number of sensors and/or detectors that can form or define at least portion of eye-vergence detection system (or subsystem) that can determine the vergence and/or change in vergence between the eyes of the subject.

Figure 8A:
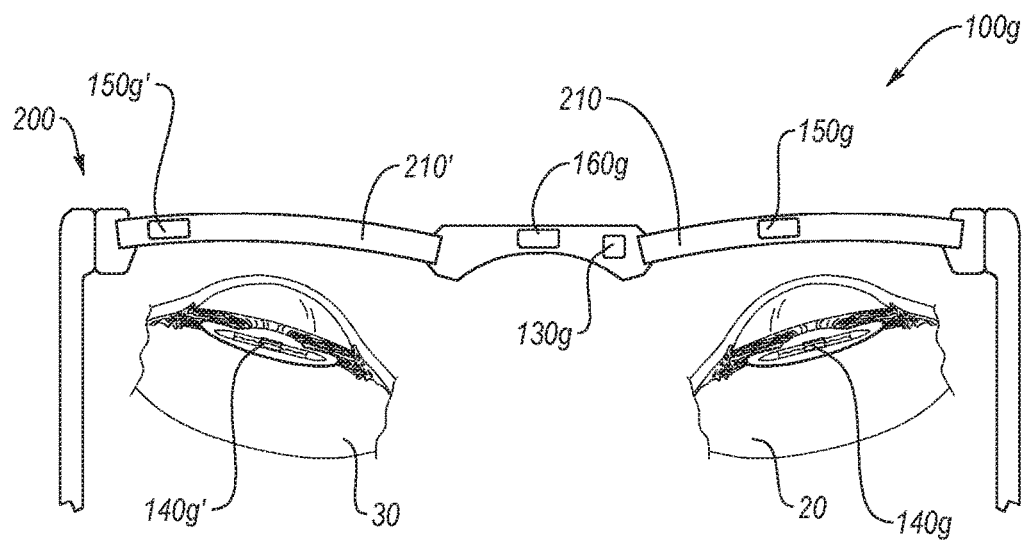
FIG. 8A is a schematic top view of a modifiable-focus lens (MFL) system according to an embodiment.

For example, as described above and illustrated in FIG. 8A, one or more elements or components that can generate an identifiable magnetic field can be secured to or integrated with a wearable device, such as glasses. FIG. 8A is a schematic top view of MFL system 100g that includes MFL device 200 (e.g., glasses), according to an embodiment. In FIG. 8A, the MFL device 200 is positioned in front of the first and second eyes 20, 30 of the subject. It should be appreciated that the right portion of the MFL device 200 (e.g., of the glasses) and/or of the MFL system can be substantially the same as the left portion (as shown in FIG. 8A) but can be a mirror image thereof. Alternatively, one portion of the MFL device 200 can be configured as shown in FIG. 8A, and another portion of the MFL device 200 can have any suitable configuration for detecting vergence between the eyes and/or movement of the right eye.

Except as otherwise described herein, the MFL system 100g and its elements and components can be similar to or the same as any of the IOL systems described herein and their corresponding elements and components. For example, the MFL device 200 can be similar to or the same as any of the IOL devices described herein. In an embodiment, the MFL device 200 can include modifiable-focus or switchable lenses 210, 210' that can be similar to or the same as the lens of any of the IOL devices described herein (e.g., switchable lenses 210 and/or 210' can include at least one material that can have electrically-modifiable index of refraction).

In an embodiment, the 200 can include one or more field sources, such as field sources 150g, 150g' that can be similar to or the same as any of the field sources described herein (e.g., similar to or the same as the field source 150 (FIGS. 4A-4B)). For example, each of the one or more field sources 150g, 150g' can be associated with or can correspond to a respective eye of the subject (e.g., field source 150g can be associated with the first eye 20 and the field source 150g' can be associated with the second eye 30), including but not limited to a magnet.

Generally, the MFL system 100g can include any suitable eye-vergence detection system. In an embodiment, the MFL system 100g can include sensors 140g, 140g' that can be mounted to the respective eyes 20, 30 of the subject. For example, one or more sensors 140g, 140g' can be implanted or secured in a haptic or an IOL device, mounted to, embedded in, or integrated with a contact lens (e.g., removable contact lens), etc. Two sensors are shown in this particular embodiment. In any event, in an embodiment, the one or more sensors 140g, 140g' can be positioned in the eyes 20, 30 or mounted thereto such that rotation or tilting of the eyes 20, 30 produces a corresponding tilting of the one or more sensors 140g, 140g' and a corresponding change in the fields sensed or detected thereby (e.g., as the fields remain substantially stationary relative to the eye sockets of the subject).

It should be appreciated that, in an embodiment, the one or more contact lenses can include the field source. For example, one or more contact lenses that can be worn by the subject can include at least one of a permanent magnet, an electromagnet, coils, etc., that can generate an identifiable magnetic and/or electric field. Moreover, the one or more of the contact lenses can include at least one switchable lens (e.g., contact lens can include a switchable lens and a non-switchable lens).

As described above in more detail, the sensors 140g, 140g' can send one or more signals to a controller 130g; the signal(s) can correspond to and/or can be at least partially based on the vergence angle and/or a change in vergence between the eyes of the subject. The MFL system 100g can include at least one communication device, such as communication device 160g, and at least one controller, such as controller 130g. The one or more sensors 140g, 140g' can be operably coupled to the controller 130g (e.g., directly or indirectly, such as via the communication device 160g). For example, the one or more sensors 140g, 140g' can wirelessly send one or more signals to the communication device 160g that can send one or more corresponding signals to the controller 130g. Alternatively, the one or more sensors 140g, 140g' can be connected directly to the controller 130g (e.g., at an I/O interface of the controller 130g).

For example, the one or more sensors 140g, 140g' can be operably coupled to the communication device 160g that can be operably coupled to the controller 130g (e.g., the same as described above in connection with the communication device 160 (FIGS. 4A-4B). In an embodiment, the one or more sensors 140g, 140g' can send one or more signals to the controller 130g. Furthermore, the controller 130g can generate and send one or more signals and/or instructions at least in part based on the signals received from the one or more sensors 140g, 140g'.

In an embodiment, the controller 130g can determine the change in the vergence between the eyes 20, 30 of the subject at least in part based on the signal(s) received from the one or more sensors 140g, 140g'. In an embodiment, the MFL device can include one or more switchable lenses (e.g., switchable lenses 210, 210'). The controller 130g can change or direct change of the focal length of the switchable lenses 210, 210'. For example, the communication device 160g can receive signals from the controller 130g and can send one or more signals to the switchable lenses 210, 210' (e.g., signals received directly or indirectly from the communication device 160g can direct a change in the focal length of the switchable lenses 210 and/or 210').

In some embodiments, the controller 130g can be mounted on or secured to the MFL device 200. For example, as mentioned above, the MFL device 200 can be configured as a pair of glasses, and the controller 130g can be mounted on or incorporated into a frame of the glasses. Alternatively, the controller 130g can be positioned outside of or external to the MFL device 200.

Generally, the switchable lenses 210, 210' can be mounted to or included in the MFL device 200, such that light entering the eyes 20, 30 passes through the switchable lenses 210, 210' before entering the eyes 20, 30. For example, the MFL device 200 can include the switchable lenses 210, 210' that can be positioned in front of the eyes 20, 30 such as to focus or redirect the light passing therethrough and entering the eyes 20, 30 to suitably focus the light on the respective retinas of the eyes 20, 30. In an embodiment, the MFL device 200 can include one or more non-switchable lenses, and the switchable lenses 210, 210' can be mounted thereto and/or integrated therewith.

As described above (e.g., in connection with switchable lenses of IOLs), the controller 130g can change or direct change of the focal length of the switchable lenses 210 and/or 210' based on the signal(s) received from the one or more sensors 140g and/or 140g' (e.g., at least in part based on the vergence angle and/or on the change in the vergence angle between the eyes 20, 30 of the subject). In particular, for example, the controller 130g can change the focal length of the switchable lenses 210 and/or 210' such as to suitably focus light on the retinas of the eyes 20, 30.

It should be appreciated that the switchable lenses 210 and/or 210' can be the only lenses in the MFL device 200. Alternatively, the switchable lenses 210 and/or 210' can be mounted on or integrated with one or more additional lenses. For example, the switchable lenses 210 and/or 210' can be mounted on or otherwise secured to existing lenses (e.g., non-switchable lenses), correction lenses, tinted lenses, polarized lenses, etc. (e.g., existing lenses of MFL device 200 that is configured as glasses).

In an embodiment, modification of the focal length of the switchable or switchable lenses 210, 210' can be tuned or trained by the subject. For example, the subject can focus on an object and can provide inputs to the controller 130g to change the focal lengths of the switchable lenses 210, 210', such as produce suitable respective focal lengths of the switchable lenses 210, 210'. Moreover, the controller can correlate the focal lengths selected by the subject the vergence angle between the eyes 20, 30 (e.g., as detected by the eye-vergence detection system). After tuning or training, the controller 130g can produce (or reproduce) the suitable focal lengths on the switchable lenses 210, 210' based on one or more signals received from the one or more sensors 140g and/or 140g'. For example, signals received from the one or more sensors 140g, 140g', which can be related thereby to a vergence that similar to or corresponds to the vergence at which the subject provided a corresponding input to the controller 130g, indicating suitable focal lengths for the switchable lenses 210, 210'.

Figure 8B:
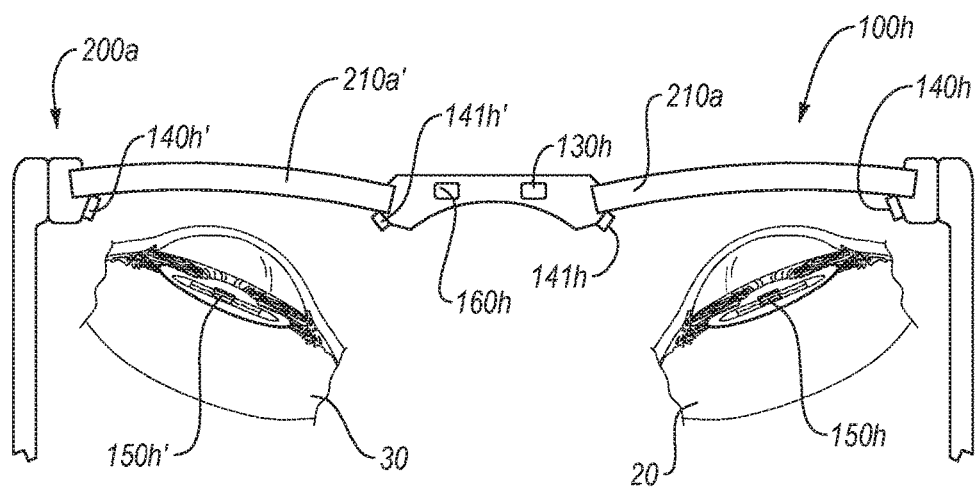
FIG. 8B is a schematic top view of an MFL system according to another embodiment.

In an embodiment, the MFL system 100g can include multiple sensors positioned in or on each of the eyes 20, 30 of the subject. Moreover, the sensors can be located on MFL device and one or more field sources can be located in or near the eye. FIG. 8B is a schematic illustration of MFL system 100h according to an embodiment. Except as otherwise described herein, the MFL system 100h and its elements and components are similar to or the same as the MFL system 100g (FIG. 8A) and its corresponding elements and components. In an embodiment, the MFL system 100h includes MFL device 200a that can have switchable lenses 210a, 210a' that can be similar to or the same as the switchable lenses 210, 210' (FIG. 8A). Moreover, the MFL system can include at least one communication device 160h and/or at least one controller 130h, which can be similar to or the same as the communication device 160g and controller 130g (FIG. 8A).

In an embodiment, the MFL system 200a can include one or more sensors 140h, 141h, 140h', 141h'. In an embodiment, the sensors 140h, 141h, 140h', 141h' can be operably coupled to the communication device 160h and to the controller 130h. Moreover, the MFL system 200a can include one or more field sources 150h, 150h' that can be mounted on or implanted in the respective eyes 20, 30 of the subject (e.g., in a similar manner as described above in connection with the one or more sensors 140g, 140g' (FIG. 8A)). The one or more field sources 150h, 150h' can establish or generate identifiable fields for the respective eyes 20, 30. In an embodiment, the one or more field sources 150h, 150h' includes a magnet. For example, as the eyes 20 and 30 pivot or tilt toward or away from each other, the change in the identifiable field produced by the one or more field sources 150h, 150h', which move relative to the one or more sensors 140h, 141h, 140h', 141h' can be detected by the one or more sensors 140h, 141h, 140h', 141h'.

The one or more sensors 140h, 141h, 140h', 141h' can generate one or more signals related to the change in the tilt of the identifiable field and to the change in the vergence between the eyes 20, 30. As described above in more detail, based on the signals received from the one or more sensors 140h, 141h, 140h', 141h', the controller 130h can determine the change in vergence between the eyes (e.g., based on the change in tilt of each of the two eyes). The controller can change or direct change of focal length of the switchable lenses 210a, 210a' (e.g., in the same manner as described above).

The eye-vergence detection system can include any number of suitable sensors and/or detectors that can facilitate determining the vergence rotation between the eyes and/or change therein. For example, the vergence detection system can include one or more forward looking detectors, such as cameras, that can track the movements of one or more eyes of the subject.

Figure 9A:
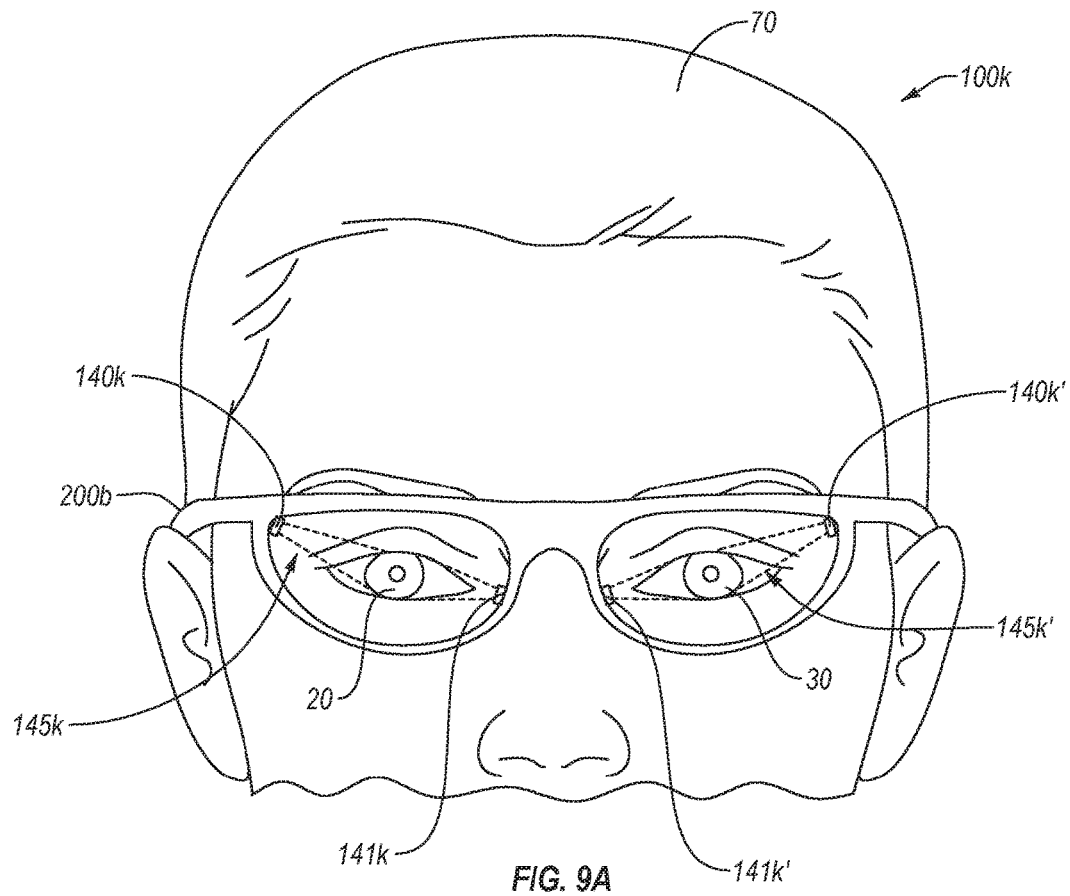
FIG. 9A is a schematic front view of an MFL system according to an embodiment.
Figure 9B:
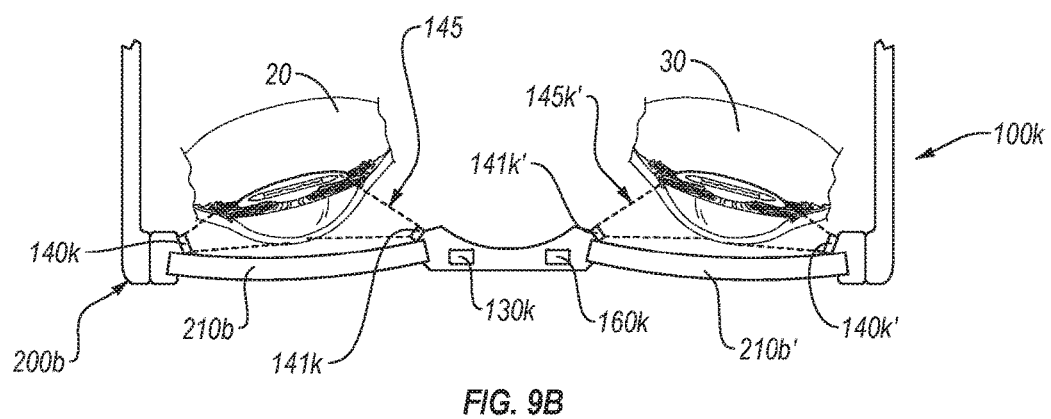
FIG. 9B is a schematic front view of an MFL system according to another embodiment.

FIGS. 9A-9B illustrate an MFL system 100k according to an embodiment. Except as otherwise described herein, the MFL system 100k and its elements and components can be similar to or the same as any of the MFL systems 100g, 100h (FIGS. 8A-8B) and their corresponding elements and components. In an embodiment, the MFL system 100k can include MFL device 200b that includes switchable lenses 210b, 210b' that can be positioned in front of the eyes 20, 30 of the subject 70.

In an embodiment, the eye-vergence detection system of the MFL system 100k can include a one or more sensor feedback loops, and can include, for example, infrared light and sensor, laser and sensor, or one or more cameras (e.g., video cameras, infrared cameras, etc.), such as cameras 140k, 141k, 140k', 141k', which can monitor movement of the eyes 20, 30. For example, the cameras 140k, 141k, 140k', 141k' can be mounted on and/or integrated with MFL device 200c. Furthermore, the cameras 140k, 141k, 140k', 141k' can be operably coupled to a controller 130k (e.g., directly or indirectly, such as via a communication device 160k) and can send one or more signals thereto. For example, the controller 130k can determine the vergence rotation between the eyes 20, 30 and/or change in vergence therebetween and can determine suitable focal lengths for switchable lenses based thereon, thereby changing the power of the switchable lenses 210b, 210b'

For example, the cameras 140k, 141k, 140k', 141k' can monitor the vergence rotation between the eyes 20, 30 and/or change in the vergence rotation. For example, video camera 140k, 141k, 140k', 141k' can have a suitable field of view (FOV), such as FOV 145k and FOV 145k' to capture movement of the respective eyes 20 and 30. As the subject moves the eyes 20 and 30 and the vergence rotation therebetween changes, the cameras 140k, 141k, 140k', 141k' can detect the movement and can send one or more signals to the controller 130k. The controller 130k can process the signal(s) received from the one or more cameras 140k, 141k, 140k', 141k' to determine the vergence rotation between the eyes 20, 30 and/or to determine a change in the vergence rotation.

For example, the one or more cameras 140k, 141k, 140k', 141k' can detect a change in the shape of each iris (or pupil) of the eyes 20, 30, as the eyes 20, 30 pivot (e.g., as a two-dimensional projection or representation of the semi-spherical iris from the vantage point of each of the cameras 140k, 141k, 140k', 141k'). In an embodiment, the controller 130k can correlate the shape or change in shape of a projection of each iris onto a plane from the vantage point of each of the cameras 140k, 141k, 140k', 141k' to a vergence rotation between the eyes 20, 30 and/or to a change in the vergence rotation. For example, the shape of the iris in the two-dimensional images produced by each of the respective cameras 140k, 141k, 140k', 141k' can change as the eyes 20, 30 pivot, and the controller 130k can correlate the shapes of the irises in the two-dimensional images from the cameras 140k, 141k, 140k', 141k' to a vergence rotation between the eyes 20, 30, thus assessing the angle of the eyes relative to each other as determined by the focal point.

It should be appreciated that the MFL system can include any suitable number of cameras. Moreover, the cameras can be positioned and oriented relative to the eyes 20, 30 of the subject in a manner that allows the controller 130k to process images therefrom to produce a three-dimensional representation of one or more of the eyes 20, 30. In an embodiment, the controller 130k can use the three-dimensional representation of the eyes 20 and/or 30 to determine the vergence rotation therebetween and/or to determine a change in the vergence rotation.

The MFL device 200 can include one or more switchable lenses, such as switchable lenses 210c, 210c'. As described above, the controller can modify or direct modification of the focal lengths of the switchable lenses 210c, 210c' based on the input received from the cameras 140k, 141k, 140k', 141k' that can be related to the vergence rotation between the eyes 20, 30.

In the example shown in FIGS. 9A-9B, the camera 140k is positioned near the bridge of the nose and the camera 141k is position opposite thereto and toward the temple of the subject 70. Analogously, cameras 140k', 141k' can have mirrored locations relative to the cameras 140k, 141k (e.g., mirrored about the nose of the subject 70). Generally, however, the cameras can be positioned and/or oriented at any suitable locations and orientations to suitably capture the movement of the eyes 20, 30. For example, the FOV 145k and/or 145k' can have generally horizontal orientations.

Figure 9C:
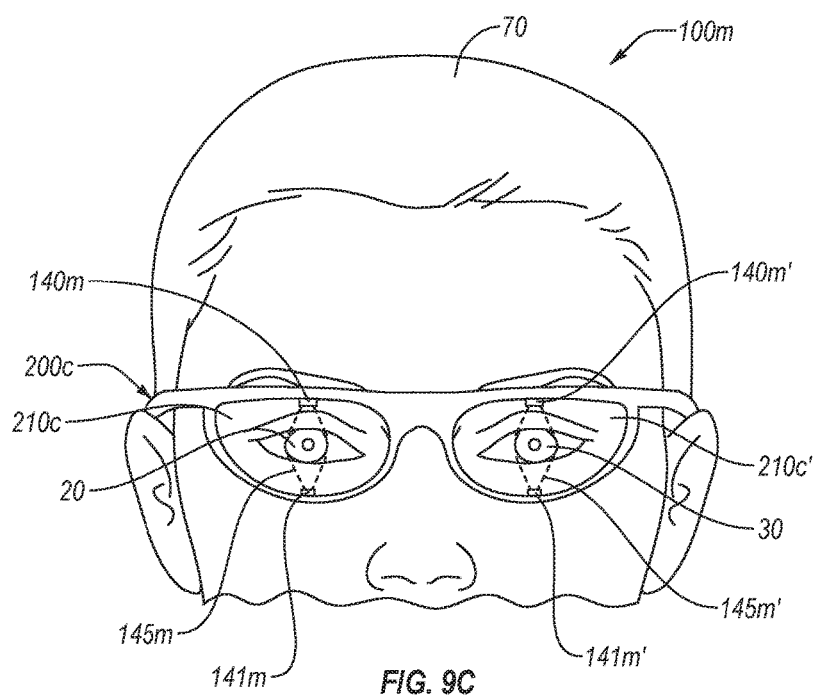
FIG. 9C is a schematic front view of an MFL system according to yet another embodiment.

FIG. 9C illustrates MFL system 100m according to an embodiment. Except as otherwise described herein, the MFL system 100m and its elements and components can be similar to or the same as the MFL system 100k (FIGS. 9A-9B) and its respective elements and components. In an embodiment, the MFL system 100m can include cameras positioned above and below the eyes 20, 30 of the subject 70. For example, the MFL system 100m can include cameras 140m, 141m that can have FOV 145m for tracking movement of the eye 20 and cameras 140m', 141m' that can have FOV 145m' for tracking movement of the eye 30. For example, the FOV 145m and/or 145m' can have generally vertical orientations.

Figure 9D:
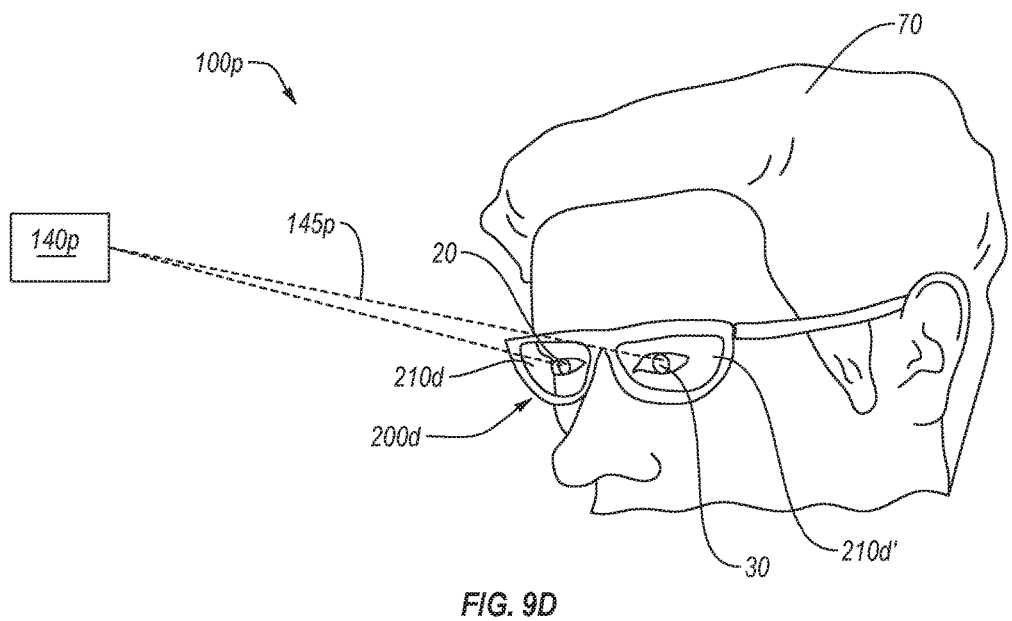
FIG. 9D is a schematic isometric view of an MFL system according to an embodiment.

In at least one embodiment, the eye-vergence detection system can include one or more cameras positioned in front of the eyes 20 and/or 30 and configured to capture movement thereof. In an embodiment, at least portion the entire eye-vergence detection system or the entire eye-vergence detection system can be positioned remotely from the subject. For example, FIG. 9D illustrates MFL system 100p that includes a detection camera 140p positioned remotely from the subject 70.

The camera 140p can have a suitable FOV 145p that can capture movement of the eyes 20, 30 and the change in the vergence therebetween. For example, the camera 140p can send one or more signals to a controller, and the controller can determine the vergence rotation or change therein based on the signal(s) received from the camera 140p.

As described above, the MFL system 100p can include MFL device 200d that can have switchable lenses 210d, 210d'. Moreover, the MFL system 100p can include a controller, and the camera 140p can be operably coupled to the controller (e.g., via a communication device). In an embodiment, the controller can change or direct changing of the focal length of the switchable lenses 210d, 210d' to a suitable focal length (e.g., based at least in part on the determined vergence between the eyes 20, 30).

In an embodiment, the camera 140p can detect light passing through the switchable lenses 210d, 210d' from the eyes 20, 30 to produce two-dimensional images. As the vergence rotation changes between the eyes 20, 30, the two-dimensional image produced by the camera 140p can change and the change can be correlated by the controller to a vergence rotation between the eyes 20, 30. Furthermore, while the images produced by the cameras described herein can be two-dimensional, it should be appreciated that the MFL system 100p can include multiple cameras that can be used to generate three-dimensional images (or digital representations thereof) and can be processed by the controller to determine the vergence between the eyes 20, 30.

In an embodiment, the camera 140p or other sensor utilizes landmarks on or in the eyeball for reference points relating to detecting vergence rotation or the angle of the eyes 20, 30, as determined by the focal point. For example, the pattern of blood vessels, or iris pattern, or other unique identifying landmarks can be used as reference points for identifying the position of the eye with regard to focal length. Moreover, it should be appreciated that the vergence rotation of the eye can be determined with any number of suitable methods, devices, and systems, such as the with one or more methods, devices, or systems described in U.S. Pat. No. 9,039,179, entitled "Unobtrusive active eye interrogation," the entire content of which is incorporated herein by this reference.

Figure 10A:
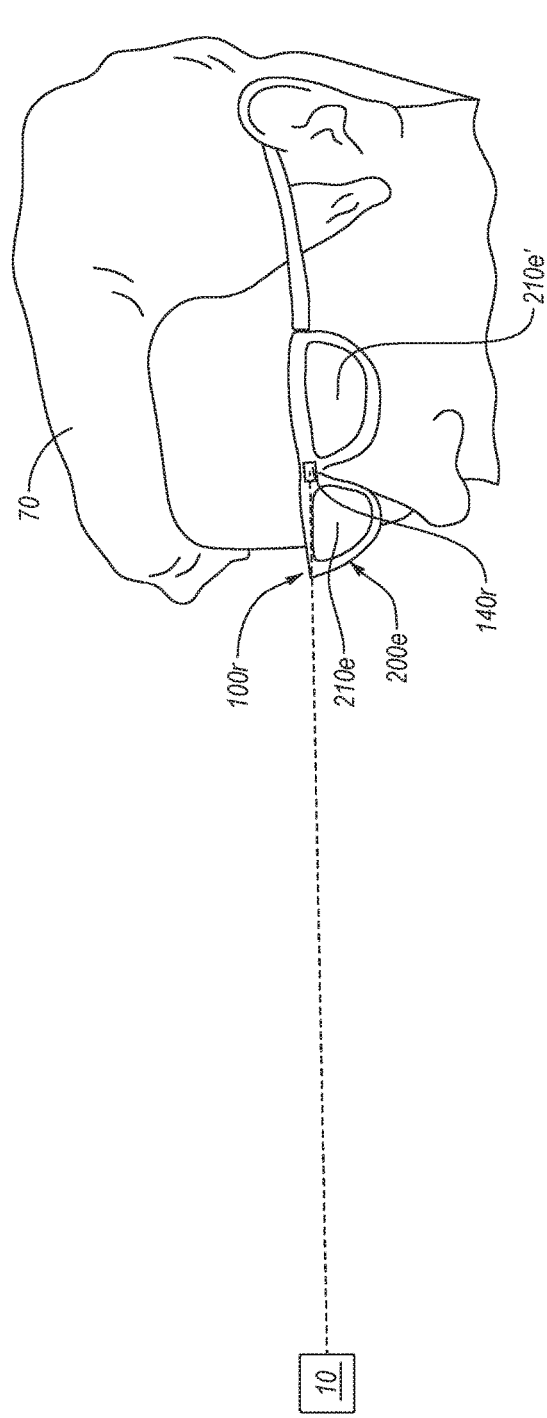
FIG. 10A is a schematic isometric view of an MFL system and a viewable object positioned a first distance from a subject according to an embodiment.
Figure 10B:
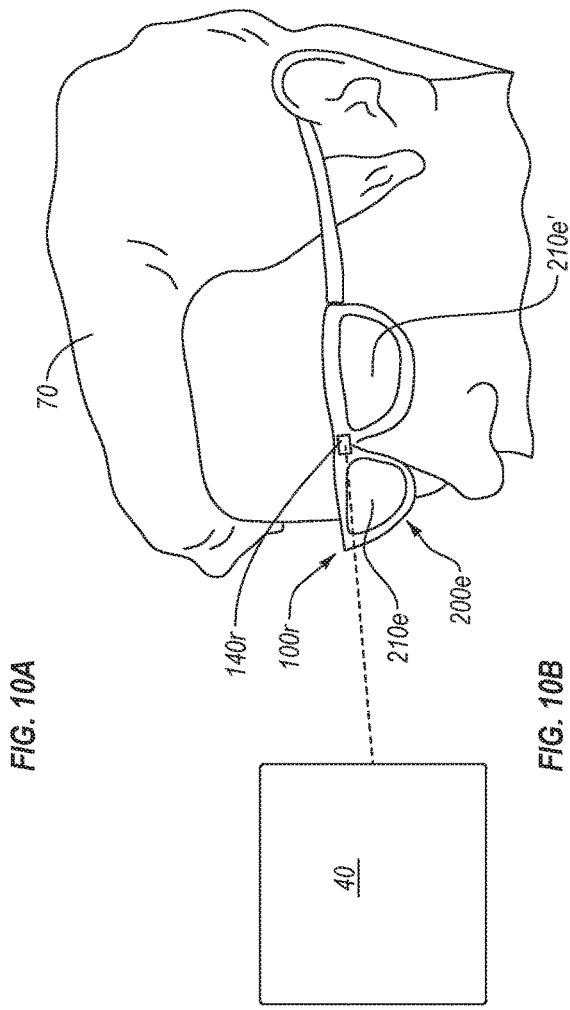
FIG. 10B is a schematic isometric view of the MFL system of FIG. 10A and a viewable object positioned at a second distance from the subject.

Additionally or alternatively, MFL system can have a range finder that can assist in determining the distance to an object being viewed by the subject and to adjust the focal length based on the distance, such that the viewed object is in focus for the subject. FIGS. 10A-10B illustrate a first object 10 at a first distance from the subject 70 and a second object 40 at a second distance from the subject 70, the second object 40 being closer to the subject 70 than the first object 10. In an embodiment, MFL system 100r can include a range finder or distance detector 140r (e.g., the distance detector 140r can include a light source and a detector that can detect reflected light and can determine distance to an object based thereon).

For example, the distance detector 140r can be positioned at any suitable location and/or orientation, such that the distance detector 140r can detect distance from the subject 70 (e.g., from the eyes of the subject 70) to the object. Moreover, the distance detector 140r can be operably coupled to a controller that can determine the distance from the subject 70 to an object (e.g., to the first and/or second objects 10, 40).

In an embodiment, the MFL system 100r can include MFL device 200e that can have switchable lenses. The controller can change the focal length of one or more of the switchable lenses based at least in part on the detected distance from the subject 70 to the object. For example, when the subject 70 looks at the object 10 (FIG. 10A), such that the MFL device 200e is generally oriented toward the object 10, the controller can determine focal length suitable for the switchable lenses based on the distance to the object 10 and can modify or direct modification of the focal length of the switchable lenses based at least in part on the distance to the object 10. For example, the subject 70 can move the MFL device 200e in a manner that aligns the distance detector 140r with the object 10. Similarly, when the subject 70 looks at the object 40 (FIG. 10B), the controller can determine focal length suitable for the switchable lenses based on the distance to the object 40 and can modify or direct modification of the focal length of the switchable lenses based at least in part on the distance to the object 40.

In an embodiment, the MFL device 200e can include switchable lenses 210e, 210e'. For example, the distance detector 140r can send one or more detection signals to a controller that can change or direct change of focal length of the switchable lenses 210e, 210e' (e.g., as described above).

Moreover, the controller can send (directly or indirectly) one or more signals to the switchable lenses 210e, 210e', directing the switching lenses 210e, 210e' to change focal length. In an embodiment, the object viewed by the subject 70 (e.g., the object 10 and/or 40) can include one or more sensors or detectors that can be configured to determine or identify the portion of the object on which the gaze of the subject is focused and can adjust the focal length based thereon. For example, the object can include a camera that can send to a controller one or more signals related to the location of the gaze of the subject. Moreover, the controller can determine gaze location onto which the eyes of the subject 70 are focused and can change or direct change of the focal length(s) of the one or more switchable lenses 210e, 210e' based the gaze location and/or based on the distance between the subject 70 and the gaze location and the subject.

For example, the object can be a personal computing devices, such as a smart phone, a tablet, a computer, etc., which can include a camera configured to track movement of the eyes of the subject 70. Furthermore, in an embodiment, the object can include the controller that can be operably coupled to the MFL device 200 and to the switchable lenses 210e, 210e' (e.g., via a wired or wireless connection), as described herein.

Generally, the distance detector 140r can be located at any suitable place, such as on or near the subject 70. In an embodiment, the MFL device 200e can have the distance detector 140r mounted thereon or incorporated therein. Alternatively or additionally, the distance detector 140r can be positioned on the subject 70 (e.g., as an implant). Moreover, any of the eye-vergence detection systems described herein can be included in the MFL system 100r. It should also be appreciated that any of the eye-vergence detection systems and/or distance detection systems can be included in an IOL system (e.g., a controller can modify the focal length of an IOL device based at least in part on the signals received from one or more eye-vergence detection systems and/or distance detection systems described herein in connection with MFL systems and devices.

As can be understood from the description herein, the switchable lenses can be adjusted for need of the subject wearing the device, depending on the focal length as set forth herein. In an embodiment, the switchable lenses can be adjusted in real-time, as the sensing feedback loop occurs, or it can be set to a specific schedule or program. In an embodiment, the system includes at least one transmitter, receiver, and/or transceiver configured to transmit or receive data related to the adjustments for a particular subject wearing the device. Thus, data related to a particular subject with specific adjustment values for a focal length (e.g., an object at distance 10 or an object at distance 40) can be transmitted to the subject itself, a database or other entity (e.g., a computing system, or another user). In this way, the real-time collection of data over time allows for collection and comparison of data that includes specific adjustment values over time for a specific subject and can indicate if the vision of that specific subject is remaining constant or improving or deteriorating, and at what rate.

Figure 11:
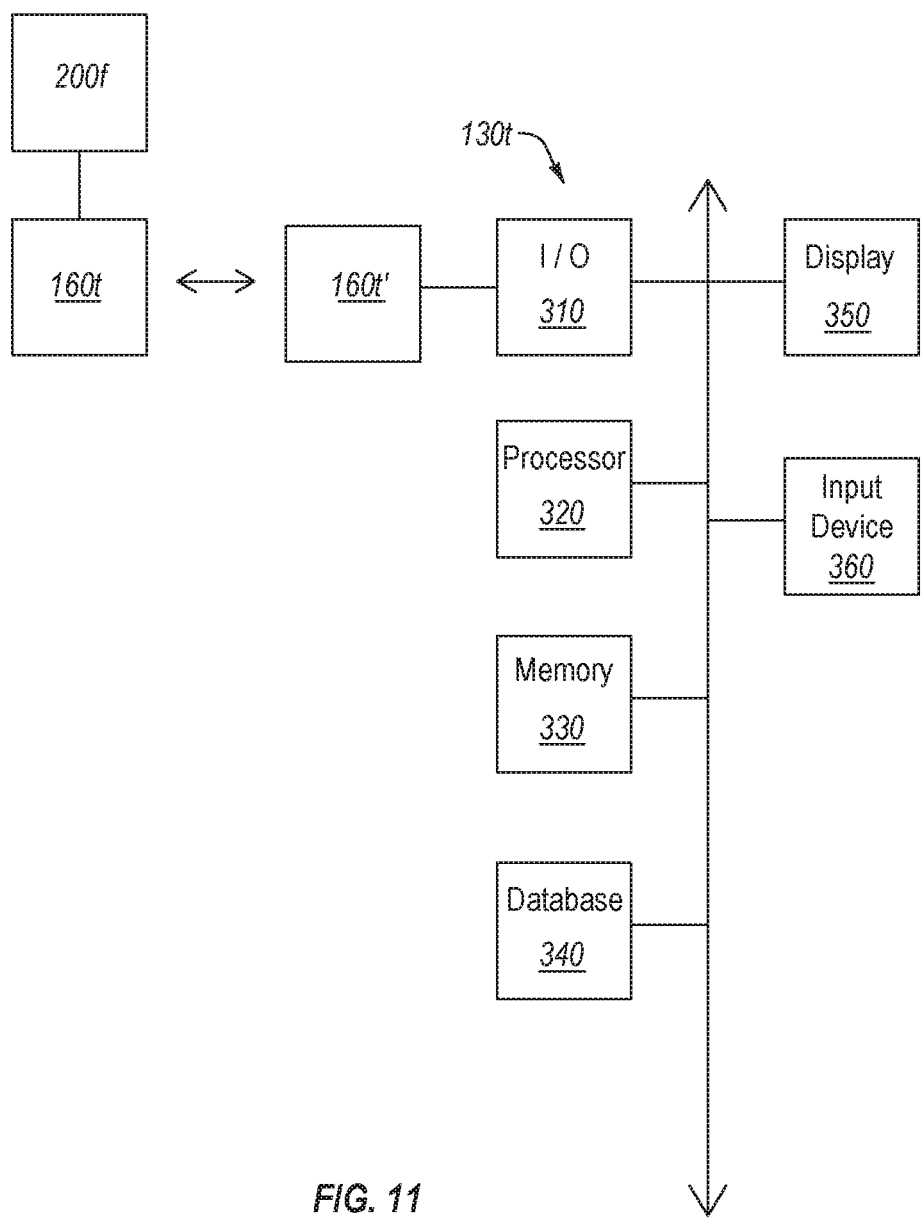
FIG. 11 is a schematic diagram of an MFL device operably coupled to a controller according to an embodiment.

For example, as shown in FIG. 11, MFL device 200f can include or can be connected to a communication device 160t (e.g., at least one receiver, transmitter, transceiver, or combinations thereof) that can receive data or instructions related to modification of the focal length(s) of one or more switchable lenses of the MFL device 200f. As described above, MFL system can include a controller 130t (e.g., the controller 130t can receive one or more signals and can determine vergence rotation of the eye and/or suitable focal length for the switchable lenses of the MFL device 200f). In an embodiment, the controller 130t can include I/O interface 310, processor 320, and memory 330 operably coupled together. In an embodiment, the controller 130t can include a database 340 (e.g., the database 340 and can have data stored in a storage memory of the controller 130t). For example, the controller 130t can store one or more parameters in the database 340 (e.g., the controller 130t can store training or tuning data in the database 340).

In an embodiment, a communication device 160t' (e.g., at least one receiver, transmitter, transceiver, or combinations thereof) can be operably coupled to the controller 130t and/or integrated therewith. For example, the communication device 160t' can be operably coupled to the communication device 160t (e.g., via wired or wireless connection), such that the MFL device 200f and the controller 130t can transmit and receive data from one another. In an embodiment, display 350 and/or input device 360 (e.g., physical or virtual keyboard, microphone, etc.) can be operably coupled to the controller 130t and/or integrated therewith. For example, a user (e.g., a subject using and/or wearing the MFL device 200f) can enter input and/or data into the controller 130t, as described herein. Moreover, it should be appreciated that the controller 130t can be operably coupled to and/or incorporated with any number of suitable devices, such as personal electronic devices (e.g., personal computers, smart phones, tablets, etc.) and/or any other computing and/or input devices. It should be appreciated that any of the systems described herein (e.g., MFL and/or IOL systems) can have a similar or the same configuration as the system described above and illustrated in FIG. 11.

It will be understood that a wide range of hardware, software, firmware, or virtually any combination thereof can be used in the controllers described herein. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more programs running on one or more processors (e.g., as one or more programs running on one or more microprocessors), as firmware, or as virtually any combination thereof. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution.

In a general sense, the various embodiments described herein can be implemented, individually and/or collectively, by various types of electro-mechanical systems having a wide range of electrical components such as hardware, software, firmware, or virtually any combination thereof; and a wide range of components that can impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein can be implemented in an analog or digital fashion or some combination thereof.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components can be referred to herein as "configured to." The reader will recognize that "configured to" or "adapted to" are synonymous and can generally encompass active-state components and/ or inactive-state components and/or standby-state components, unless context requires otherwise.

While particular aspects of the present subject matter described herein have been shown and described, it will be apparent that, based upon the teachings herein, changes and modifications can be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would include but not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, any recited operations therein can generally be performed in any order. Examples of such alternate orderings can include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, the various aspects and embodiments disclosed herein are for purposes of illustration and are not intended to be limiting, with the true scope and spirit being indicated by the following claims.

What is claimed is:

1. A system, comprising:
    an eye-vergence detection system configured to detect at least one of a vergence rotation between a first eye and a second eye of a subject or a change in the vergence rotation between the first eye and the second eye of the subject and to generate one or more detection outputs corresponding thereto, the eye-vergence detection system including:
        a field source associated with the first eye that is configured to be positioned on the subject, the field source configured to establish an identifiable field; and
        a sensor associated with the second eye that is configured to detect a change in the identifiable field established by the field source;
    a switchable lens configured to selectively switch between a first focal length and at least a second focal length that is less than the first focal length; and
    a controller operably coupled to the eye-vergence detection system to receive the one or more detection outputs therefrom, the controller configured to detect the vergence rotation or changes in the vergence rotation by distinguishing a first portion of a rotation between the first eye and the second eye from a second portion due to a co-tilt rotation of both the first eye and the second eye, the controller including control electrical circuitry configured to direct the switchable lens to selectively switch between the first focal length and the second focal length responsive to the one or more detection outputs.

2. The system of claim 1, wherein at least a portion of the eye-vergence detection system is removably positionable on a subject.

3. The system of claim 1, wherein at least a portion of the eye-vergence detection system is positionable remotely from the subject.

4. The system of claim 1, wherein the sensor is configured to detect the change of the vergence rotation between the first eye and the second eye of the subject, the sensor configured to generate the one or more detection outputs on the detected change.

5. The system of claim 1, wherein the field source is configured to establish the identifiable field having a predetermined orientation relative to at least one of the first eye or the second eye of the subject.

6. The system of claim 5, wherein the identifiable field is a magnetic field.

7. The system of claim 6, wherein the sensor is configured to detect a change in the established identifiable magnetic field corresponding to the change the vergence rotation between the first eye and the second eye of the subject.

8. The system of claim 6, wherein the at least one sensor is configured to detect a change corresponding to the vergence rotation by detecting a changed component of the field source in a direction substantially perpendicular to a direction of a dominant component of the field source.

9. The system of claim 1, wherein the field source is configured to be removably positioned on the subject.

10. The system of claim 9, wherein the field source is included in glasses wearable by the subject.

11. The system of claim 1, wherein the switchable lens is included in glasses wearable by the subject.

12. The system of claim 11, wherein the glasses include at least one non-switchable lens and the switchable lens is mounted to or integrated with the at least one non-switchable lens.

13. The system of claim 1, wherein the sensor is configured to be mounted on at least one of the first eye or the second eye or implanted in at least one of the first eye or the second eye of the subject.

14. The system of claim 1, wherein the sensor is configured to be positioned externally to the first eye and the second eye.

15. The system of claim 14, wherein the sensor is configured to be removably positioned on the subject.

16. The system of claim 15, wherein the sensor is included in glasses wearable by the subject.

17. The system of claim 1, further comprising a communication device that operably couples the sensor to the controller.

18. The system of claim 1, wherein the eye-vergence detection system further includes:
an additional sensor configured to be positioned externally to one or more of the first eye and the second eye and configured to detect a change in an additional identifiable field corresponding to the vergence rotation between the first eye and the second eye, and to generate one or more additional detection outputs at least partially based on the detected change.

19. The system of claim 18, further comprising an additional switchable lens configured to selectively switch between a first focal length and at least a second focal length that is less than the first focal length.

20. The system of claim 19, further comprising an additional controller to receive the one or more additional detection outputs, the additional controller including additional control electrical circuitry configured to direct the additional switchable lens to selectively switch between the first focal length and the at least a second focal length responsive to the additional detection output.

21. The system of claim 1, wherein the eye-vergence detection system includes at least one camera configured to have a field of view that captures movement of at least one of the first eye or the second eye of the subject and to generate the one or more detection outputs in response thereto.

22. The system of claim 21, wherein the at least one camera is mounted to glasses wearable by the subject.

23. The system of claim 22, wherein the at least one camera includes two cameras positioned about the first eye and having a generally horizontally oriented field of view.

24. The system of claim 22, wherein the at least one camera includes two additional cameras positioned about the second eye and having a generally horizontally oriented field of view.

25. The system of claim 22, wherein the at least one camera includes two cameras positioned about the first eye and having a generally vertically oriented field of view.

26. The system of claim 25, wherein the at least one camera includes two additional cameras positioned about the second eye and having a generally vertical oriented field of view.

27. The system of claim 1, wherein the passive sensor includes at least one of a microelectromechanical-based sensor, a hall effect sensor, a magnetoresistance sensor, a magneto-diode, a Lorentz forced-based sensor, or an electron tunneling-based sensor.

28. The system of claim 1, wherein at least one of the first field source or the second field source includes a permanent magnet.

29. A system, comprising:
an eye-vergence detection system including:
a first field source removably positionable on a subject and configured to establish a first identifiable magnetic field, the first field source associated with a first eye of the subject;
a second field source removably positionable on the subject and configured to establish a second identifiable magnetic field, the second field source associated with a second eye of the subject, the second field source configured to establish the second identifiable magnetic field oriented at an oblique or perpendicular angle relative to the first identifiable magnetic field;
at least one sensor configured to detect a change in at least one of the first identifiable magnetic field or the second identifiable magnetic field in response to a change in a vergence rotation between the first eye and the second eye of the subject and to generate one or more detection outputs in response thereto;
at least one switchable lens configured to selectively switch between a first focal length and at least a second focal length that is less than the first focal length; and
a controller operably coupled to the eye-vergence detection system to receive the one or more detection outputs therefrom, the controller configured to detect the vergence rotation or changes in the vergence rotation by distinguishing a first portion of a rotation between the first eye and the second eye from a second portion due to a co-tilt rotation of both the first eye and the second eye, the controller including control electrical circuitry configured to direct the switchable lens to selectively switch between the first focal length and the second focal length responsive to the one or more detection outputs.

30. The system of claim 29, wherein the at least one sensor is configured to be implanted in the first eye or the second eye of the subject.

31. The system of claim 29, wherein the at least one sensor is configured to be removably positioned on the subject.

32. The system of claim 31, further comprising at least one contact lens and the at least one sensor is mounted to or integrated with the at least one contact lens.

33. The system of claim 31, further comprising at least one contact lens, and at least one of the first field source or the second field source is mounted to or integrated with the at least one contact lens.

34. The system of claim 29, wherein at least one of the first field source or the second field source is mounted to or integrated with glasses wearable by the subject.

35. The system of claim 34, wherein the glasses include the at least one switchable lens.

36. The system of claim 35, wherein the glasses include at least one non-switchable lens, and the at least one switchable lens is mounted to or integrated with the at least one non-switchable lens.

37. The system of claim 29, wherein at least a portion of the eye-vergence detection system is positioned remotely from the subject.

38. The system of claim 29, wherein the at least one sensor is mounted to or integrated with glasses wearable by the subject.

39. The system of claim 38, wherein the glasses include the at least one switchable lens.

40. The system of claim 39, wherein the glasses include at least one non-switchable lens, and the at least one switchable lens is mounted to or integrated with the at least one non-switchable lens.

41. The system of claim 29, wherein the first field source includes a dipole magnetic field component oriented substantially parallel to an optical axis of the first eye, and the second field source includes an additional dipole magnetic field component oriented substantially parallel to an axis extending between the first eye and the second eye.

42. The system of claim 29, wherein the at least one sensor includes:
a first sensor configured to detect a change in the first identifiable magnetic field in response to a change in a vergence rotation between the first eye and the second eye of the subject and to generate the one or more detection outputs at least partially based on the detected change;
a second sensor configured to detect a change in the second identifiable magnetic field in response to a change in a vergence rotation between the first eye and the second eye of the subject and to generate one or more additional detection outputs at least partially based on the detected change;
wherein a first detection output of the one or more detection outputs at least partially corresponds to a changed component of the first identifiable magnetic field in a direction substantially perpendicular to the direction of a dominant component of the identifiable magnetic field;
wherein a second detection output of the one or more additional detection outputs at least partially corresponds to a changed component of the second identifiable magnetic field in a direction substantially perpendicular to the direction of the dominant component of the second identifiable magnetic field; and
wherein the controller is configured to distinguish a first portion of the rotation due to the vergence rotation between the first eye and the second eye from a second portion due to a co-tilt rotation of both the first eye and the second eye at least partially based on a comparison of the first detection output and the second detection output.

43. A method, comprising:
an eye-vergence detection system:
establishing an identifiable field with a field source associated with a first eye of a subject; and
detecting a change in the identifiable field with a sensor associated with a second eye of the subject and at least one of a vergence rotation between the first eye and the second eye of a subject or a change in the vergence rotation between the first eye and the second eye of the subject and generating one or more detection outputs corresponding thereto;
a switchable lens selectively switching between a first focal length and at least a second focal length that is less than the first focal length; and
a controller operably coupled to the eye-vergence detection system and receiving the one or more detection outputs therefrom, the controller detecting the vergence rotation or changes in the vergence rotation by distinguishing a first portion of a rotation between the first eye and the second eye from a second portion due to a co-tilt rotation of both the first eye and the second eye, the controller including control electrical circuitry directing the switchable lens to selectively switch between the first focal length and the second focal length responsive to the one or more detection outputs.

44. The method of claim 43, wherein at least a portion of the eye-vergence detection system is removably positionable on a subject.

45. The method of claim 43, wherein the field source establishes the identifiable field having a predetermined orientation relative to at least one of the first eye or the second eye of the subject.

46. The method of claim 45, wherein the sensor detects a change in the established identifiable field corresponding to the change in the vergence rotation between the first eye and the second eye of the subject.

47. The method of claim 45, wherein the field source is included in glasses wearable by the subject.

48. The method of claim 43, wherein the eye-vergence detection system includes at least one camera capturing movement of at least one of the first eye or the second eye of the subject and generating the one or more detection outputs in response thereto.

49. The method of claim 48, wherein the at least one camera is mounted to glasses wearable by the subject.

* * * * *